(12) United States Patent
Chen et al.

(10) Patent No.: US 7,329,495 B2
(45) Date of Patent: Feb. 12, 2008

(54) MUTATIONS IN KIT CONFER IMATINIB RESISTANCE IN GASTROINTESTINAL STROMAL TUMORS

(75) Inventors: Lei L. Chen, Pearland, TX (US); Marsha L. Frazier, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 11/148,770

(22) Filed: Jun. 9, 2005

(65) Prior Publication Data

US 2006/0019280 A1  Jan. 26, 2006

Related U.S. Application Data

(60) Provisional application No. 60/578,403, filed on Jun. 9, 2004.

(51) Int. Cl.
  *C12Q 1/68* (2006.01)
(52) U.S. Cl. .......................................................... 435/6
(58) Field of Classification Search .................... 435/6
  See application file for complete search history.

(56) References Cited

U.S. PATENT DOCUMENTS

| | | |
|---|---|---|
| 5,583,110 A | 12/1996 | Altchek et al. |
| 5,889,159 A | 3/1999 | Chen et al. |
| 5,972,628 A | 10/1999 | Eigenbrodt et al. |
| 5,998,151 A | 12/1999 | Johnston et al. |
| 6,326,161 B1 | 12/2001 | Puscas et al. |
| 6,331,402 B1 | 12/2001 | Nussbaum et al. |
| 6,339,100 B1 | 1/2002 | Longley |
| 6,472,157 B1 | 10/2002 | Di Rienzo et al. |
| 6,576,423 B2 | 6/2003 | Batra et al. |
| 6,645,972 B2 | 11/2003 | Jolivet et al. |
| 6,656,684 B1 | 12/2003 | Sandler |
| 2002/0150877 A1* | 10/2002 | Augustus .................... 435/4 |
| 2003/0045451 A1 | 3/2003 | Bacus |
| 2003/0064397 A1 | 4/2003 | Spancake et al. |
| 2003/0068311 A1 | 4/2003 | Lasek et al. |
| 2003/0086924 A1 | 5/2003 | Sliwkowski |
| 2003/0087317 A1 | 5/2003 | Bandman et al. |
| 2003/0118579 A1 | 6/2003 | Walker et al. |
| 2003/0147813 A1 | 8/2003 | Lyons |
| 2003/0148955 A1 | 8/2003 | Pluenneke |
| 2003/0158105 A1 | 8/2003 | Sawyers et al. |
| 2003/0190688 A1 | 10/2003 | Crosby et al. |
| 2003/0199002 A1 | 10/2003 | Siegfried et al. |
| 2003/0203846 A1 | 10/2003 | Srivastava et al. |
| 2003/0215528 A1 | 11/2003 | Graham et al. |
| 2003/0235561 A1 | 12/2003 | Vandenburgh et al. |
| 2004/0001835 A1 | 1/2004 | Woessner et al. |
| 2004/0005623 A1 | 1/2004 | Longley |
| 2004/0013667 A1 | 1/2004 | Kelsey et al. |
| 2004/0018188 A9 | 1/2004 | Walker et al. |
| 2004/0029815 A1 | 2/2004 | Tidmarsh et al. |

FOREIGN PATENT DOCUMENTS

| | | |
|---|---|---|
| WO | WO-2002102976 | 12/2002 |
| WO | WO-2003018768 | 3/2003 |
| WO | WO-2003043591 | 5/2003 |
| WO | WO-2003065995 | 8/2003 |
| WO | WO-2003068265 | 8/2003 |
| WO | WO-2003073998 | 9/2003 |
| WO | WO-2003074082 | 9/2003 |
| WO | WO-2003075741 | 9/2003 |
| WO | WO-2003075957 | 9/2003 |
| WO | WO-2003076424 | 9/2003 |
| WO | WO-2003077841 | 9/2003 |
| WO | WO-2003082301 | 10/2003 |
| WO | WO-2003090686 | 11/2003 |
| WO | WO-2003105773 | 12/2003 |
| WO | WO-2004004644 | 1/2004 |
| WO | WO-2004008099 | 1/2004 |
| WO | WO-2004012746 | 2/2004 |
| WO | WO-2004012769 | 2/2004 |

OTHER PUBLICATIONS

Tockman et al (Cancer Res., 1992, 52:2711s-2718s).*
Hemsley et al (Nucleic Acids Research, 1989, 17(16):6545-6551).*
Benjamin et al., "Phase III dose-randomized study of imatinib mesylate (ST1571) for GIST: Intergroup S0033 early results," Presentation, 2003 ASCO Annual Meeting, 2003.
Branford et al., "Detection of *BCR-ABL* mutations in patients with CML treated with imatinib is virtually always accompanied by clinical resistance, and mutations in the ATP phosphate-binding loop (P-loop) are associated with a poor prognosis," *Blood*, 102(1): 276-283, 2003.
Chan et al., "Autoinhibition of the Kit Receptor Tyrosine Kinase by the Cytosolic Juxtamembrane Region," *Mol. Cell. Biol.*, 23(9): 3067-3078, 2003.
Chen et al., "A Missense Mutation in KIT Kinase Domain 1 Correlates with Imatinib Resistance in Gastrointestinal Stromal Tumors," *Cancer Res.*, 64: 5913-5919, 2004.
Connolly et al., "Gastrointestinal stromal tumours," *Br. J. Surg.*, 90(10): 1178-1186, 2003.
Corless et al., "*KIT* Mutations Are Common in Incidental Gastrointestinal Stromal Tumors One Centimeter or Less in Size," *Am. J. Pathol.*, 160(5): 1567-1572, 2002.
Dei Tos, "The reappraisal of gastrointestinal stromal tumors: from Stout to the KIT revolution," *Virchows Arch*, 442: 421-428, 2003.

(Continued)

*Primary Examiner*—Misook Yu
*Assistant Examiner*—Sean E Aeder
(74) *Attorney, Agent, or Firm*—Fulbright & Jaworski L.L.P.

(57) ABSTRACT

The present invention relates to methods and compositions concerning resistance to a drug for cancer comprising aberrant KIT signal, such as aberrant KIT sequence or expression. In a specific embodiment, the cancer is also initially responsive to imatinib therapy, such as in gastrointestinal stromal tumors (GISTs). In particular embodiments, a mutation in a KIT polynucleotide confers resistance to imatinib treatment, and in specific embodiments the exemplary mutation is at 1982T→C. Thus, the invention provides a means to adjust for or circumvent the resistance to imatinib drug treatment.

12 Claims, 11 Drawing Sheets

OTHER PUBLICATIONS

Demetri et al., "Clinical activity and tolerability of the multi-targeted tyrosine kinase inhibitor SU11248 in patients (pts) with metastatic gastrointestinal stromal tumor (GIST) refractory to imatinib mesylate," Presentation, 2003 ASCO Annual Meeting, 2003.

Demetri et al., "Efficacy and Safety of Imatinib Mesylate in Advanced Gastrointestinal Stromal Tumors," *N. Engl. J. Med.*, 347(7): 472-480, 2002.

Demetri, "Identification and treatment of chemoresistant inoperable or metastatic GIST: experience with the selective tyrosine kinase inhibitor imatinib mesylate," *Eur. J. Cancer*, 38(Suppl. 5): S52-59, 2002.

Eisenberg et al., "Pharmacotherapy of gastrointestinal stromal tumours," *Expert Opin. Pharmacother.*, 4(6): 869-74, 2003.

Fabbro et al., "Protein kinases as targets for anticancer agents: from inhibitors to useful drugs," *Pharmacol. Ther.*, 93(2-3): 79-98, 2002.

Fletcher et al., "Mechanisms of resistance to imatinib mesylate (IM) in advanced gastrointestinal stromal tumor (GIST)," Presentation, 2003 ASCO Annual Meeting, 2003.

Giuli, "Gastrointestinal Stromal Tumors," Review article, School of General and Emergency Surgery, University of Siena, Italy, 2001.

Heikki et al., "Brief Report: Effect of the Tyrosine Kinase Inhibitor ST1571 in a Patient with a Metastatic Gastrointestinal Stromal Tumor," *N. Engl. J. Med.*, 344(14): 1052-1056, 2001.

Heinrich et al., "Kinase Mutations and Imatinib Response in Patients With Metastatic Gastrointestinal Stromal Tumor," *J. Clin. Oncol.*, 21: 4342-4349, 2003.

Heinrich et al., "PDGFRA activating mutations in gastrointestinal stromal tumors," *Science*, 299(5607): 708-10, 2003.

Heinrich et al., "PDGFRA and *KIT* mutations correlate with the clinical responses to imatinib mesylate in patients with advanced gastrointestinal stromal tumors (GIST)," 2003 ASCO Annual Meeting, 2003.

Hirota et al., "Familial gastrointestinal stromal tumors associated with dysphagia and novel type germline mutation of KIT gene," *Gastroenterology*, 122(5): 1493-9, 2002.

Hirota et al., "Gain-of Function Mutations of c-*kit* in Human Gastrointestinal Stromal Tumors," *Science*, 279: 577-580, 1998.

Hirota et al., "Gain-of-function mutation at the extracellular domain of KIT in gastrointestinal stromal tumours," *J. Pathol.*, 193(4): 505-510, 2001.

Hirota et al., "Gain-of-function mutations of patelet-derived growth factor receptor alpha gene in gastrointestinal stromal tumors," *Gastroenterology*, 125(3): 660-7, 2003.

Jafri et al., "Mechanisms of Metastasis as Related to Receptor Tyrosine Kinases in Small-Cell Lung Cancer," *JEPTO*, 22(3): 147-165. 2003.

Kinoshita et al., "c-kit gene mutation of exon 17 or 13 is very rare in sporadic gastrointestinal stromal tumors," *J. Gastrogenterol. Hepatol.*, 18(2): 147-51, 2003.

Kitamura et al., "Gastrointestinal stromal tumors (GIST): A model for molecule-based diagnosis and treatment of solid tumors," *Cancer Sci.*, 94(4): 315-320, 2003.

Lasota et al., "Mutations in Exon 11 of c-Kit Occur Preferentially in Malignant *versus* Benign Gastrointestinal Stromal Tumors and Do Not Occur in Leiomyomas or Leiomyosarcomas," *Am. J. Pathol.*, 154(1): 53-60, 1999.

Lasota et al., "Mutations in Exons 9 and 13 of *KIT* Gene Are Rare Events in Gastrointestinal Stromal Tumors," *Am. J. Pathol.*, 157(4): 1091-1095, 2000.

Lux et al., "KIT Extracellular and Kinase Domain Mutations in Gastrointestinal Stromal Tumors," *Am. J. Pathol.*, 156(3): 791-795, 2000.

Ma et al., "Inhibition of Spontaneous Receptor Phosphorylation by Residues in a Putative α-Helix in the KIT Intracellular Juxtamembrane Region," *J. Biol. Chem.*, 274(19): 13399-13402.

Ma et al., "The c-*KIT* mutation causing human mastocytosis is resisant to STI1571 and other KIT kinase inhibitors; kinases with enzymatic site mutations show different inhibitor sensitivity profiles than wild-type kinases and those with regulatory-type mutations," *Blood*, 99(5): 1741-1744, 2002.

Manley et al., "Imatinib: a selective tyrosine kinase inhibitor," *Eur. J. Cancer*, 38(Suppl. 5): S19-27, 2002.

O'Farrell et al., "SU11248 is a novel FLT3 tyrosine kinase inhbitor with potent activity in vitro and in vivo," *Blood*, 101(9): 3597-3605, 2003.

Rasponllini et al., "c-KIT expression and correlation with chemotherapy resistance in ovarian carcinoma: an immunocytochemical study," *Annals of Oncology*, 15: 594-597, 2004.

Rubin et al., "KIT Activation is a Ubiquitous Feature of Gastrointestinal Stromal Tumors," *Cancer Res.*, 61: 8118-8121, 2001.

Sakurai et al., "Mutations in c-*kit* Gene Exons 9 and 13 in Gastrointestinal Stromal Tumors among Japanese," *Jpn. J. Cancer Res.*, 92: 494-498, 2001.

Sattler et al., "Targeting c-Kit mutations: basic science to novel therapies," *Leukemia Research*, 28S1: S11-S20, 2004.

Singer et al., "Prognostic Value of *KIT* Mutation Type, Mitotic Activity, and Histologic Subtype in Gastrointestinal Stromal Tumors," *J. Clin. Oncol.*, 20(18): 3898-3905, 2002.

Sommer et al., "Gastrointestinal stromal tumors in a mouse model by targeted mutation of the Kit receptor tyrosine kinase," *PNAS*, 100(11): 6706-6711, 2003.

Takeshima et al., "A review of soluble c-kit (s-kit) as a novel tumor marker and possible molecular target for the treatment of CNS germinoma," *Surg. Neurol.*, 60(4): discussion 324-5, 2003.

Tamborini et al., "A New Mutation in the KIT ATP Pocket Causes Acquired Resistance to Imatinib in a Gastrointestinal Stromal Tumor Patient," *Gastroenterology*, 127: 294-299, 2004.

Tamborini et al., "*KITN*al$^{654}$ Ala Receptor Detected in One Imatinib-Resistant GIST Patient," *Cancer Res.*, 65(3): 1115, 2005.

Tipping et al., "Comparative gene expression profile of chronic myeloid leukemia cells innately resistant to imatinib mesylate," *Exp. Hematology*, 31: 1073-1080, 2003.

Tuveson et al., "STI571 inactivation of the gastrointestinal stromal tumor c-KIT oncoprotein: biological and clinical implications," *Oncogene*, 20: 5054-5058, 2001.

Van Glabbeke et al., "Prognostic factors of toxicity and efficacy in patients with gastro-intestinal stromal tumors (GIST) treated with imatinib: A study of the EORTC-STBSG, ISG and AGITG," Presentation, 2003 ASCO Annual Meeting, 2003.

Verweij et al., "Early efficacy comparison of two doses of imatinib for the treatment of advanced gastrointestinal stromal tumors (GIST): Intereim results of a randomized phase III trial from the EORTC-STBSG, ISG and AGITG," Presentation, 2003 ASCO Annual Meeting, 2003.

Van Oosterom et al., "Safety and efficacy of imatinib (STI571) in metastatic gastrointestinal stromal tumours: a phase I study," *The Lancet*, 358: 1421-23, 2001.

Von Mehren, "Recent Advances in the Management of Gastrointestinal Stromal Tumors," *Curr. Oncol. Reports*, 5: 288-294, 2003.

Wakai et al., "Late resistance to imatinib therapy in a metastatic gastrointestinal stromal tumour is associated with a second KIT mutation," *Br. J. Cancer*, 90: 2059-2061, 2004.

\* cited by examiner

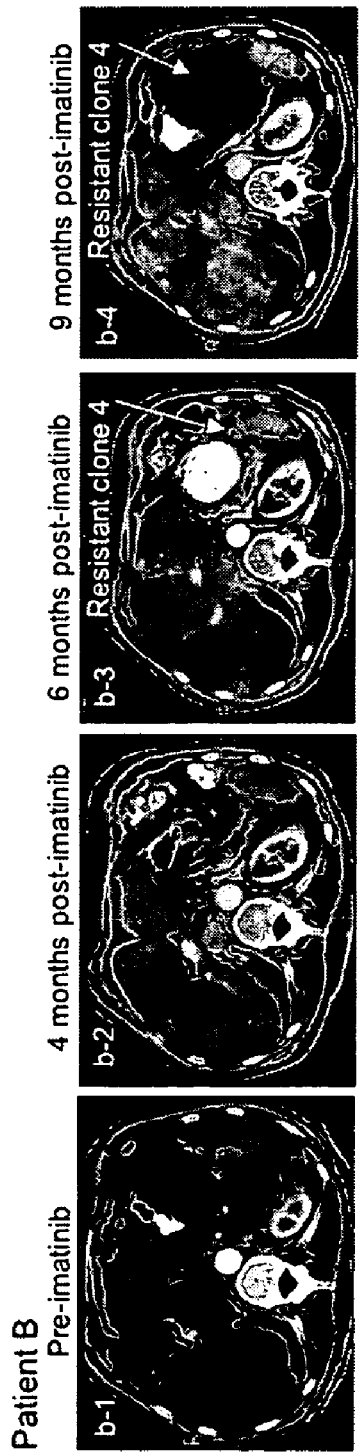
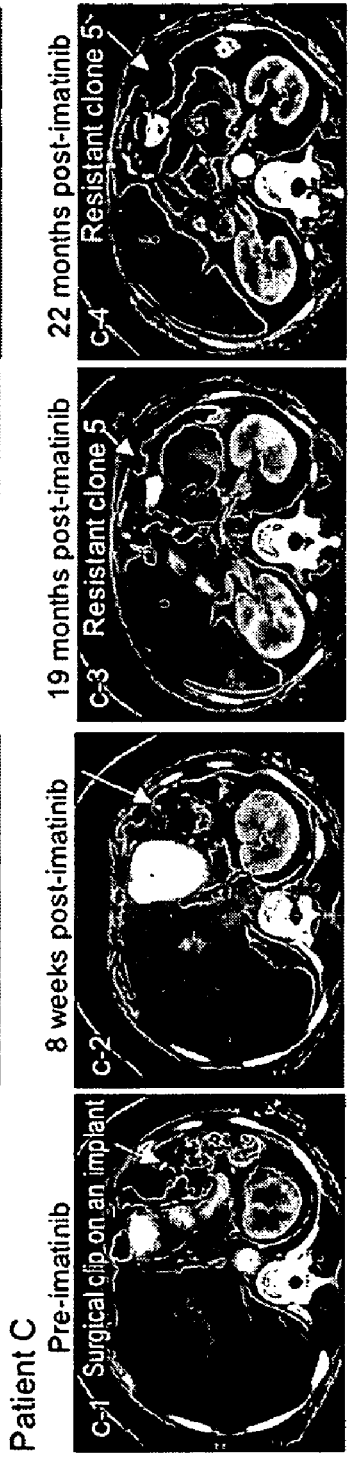
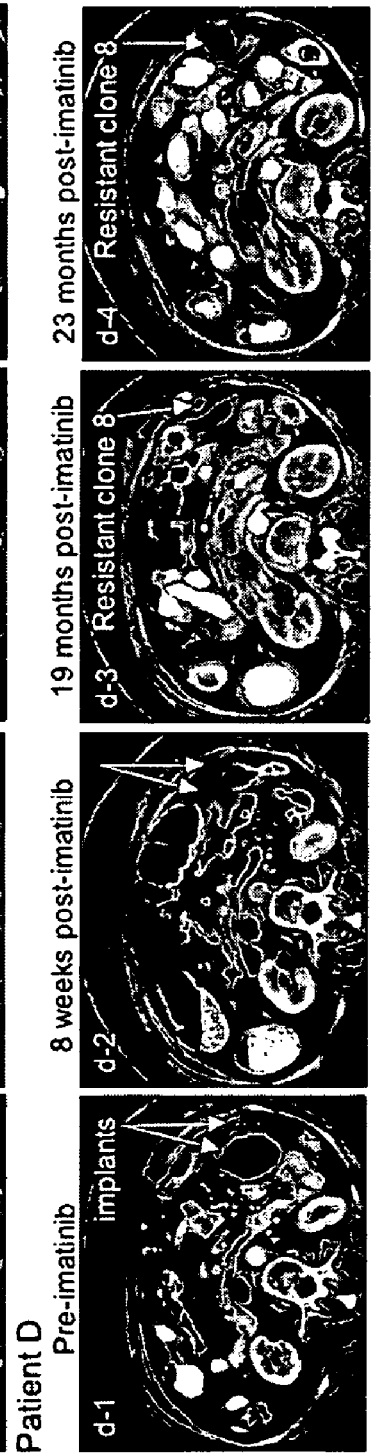
FIG. 1B
FIG. 1C
FIG. 1D

```
.........Intron 12 of KIT.....................................
aactgcttat ggcttaatta agtcagatgc ggccatgact gtcgctgtaa agatgctcaa
                       FO →
gcgtaagttc ctgtatggta ctgcatgcgc ttgacatcag tttgccagtt gtgcttttg ctaaaatgca tgtttccaat tttagCGAGT GCCCATTTGA CAGAACGGGA AGCCCTCATG
                              Mutation-FI →            C
TCTGAACTCA AAGTCCTGAG TTACCTTGGT AATCACATGA ATATTGTGAA TCTACTTGGA
                       WILD TYPE-FI →
GCCTGCACCA TTGGAGgtaa agccgtgtcc aagctgcctt ttattgtctg tcaggttatc aaaacatgac attttaatat gattttggca atgctagatt ataaactgct tggaagattt
                                                    ← RIO
ttttacccag actgttgttc tctcttgcta gattttgttt tcctcattgt tcttaagaat
....................................Intron 13 of KIT..........
```

FIGURE 7

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ttcctggagg ggtgacccaa acact                                           25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
cccaagtgtt ttatgtatttt                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
atggtgtgat gcatgtatta                                                 20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tccagagtgc tctaatgac                                                  19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aggtggaaca aaacaaagg                                                  19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
```

```
tactgcatgc gcttgacatc                                              20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
ccaagcagtt tataatctag c                                            21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
ttctacatgt cccacttgat t                                            21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
agcatgatat acatactctc tg                                           22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
gtgaacatca ttcaaggcgt                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
cctttgcagg actgtcaagc a                                            21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
```
tcctgactta cgacaggctc gt                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
acatcatgcc agctacgatt                                                 20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
acaccctgtt cactcctttg ctga                                            24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gactcctttg aatgcagaag a                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cgtgattcat ttatttgttc                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
catccacttc acaggtagtc                                                 20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ttcacagaga cttggcagcc ag                                              22

```
<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ttcctggagg ggtgacccaa acact                                           25

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ctggtgctgt tggtgattgt                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
tgttccttca accaccttcc                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gcagctgcct tatgactcaa                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
tgaggctgga cgatcataga                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
aaccctgctg atgaaagcac                                                 20
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ggttgtcaaa gatgctctca gg                                              22

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ccttggtaat cacatgaata ttgc                                            24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ccaagcagtt tataatctag c                                               21

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
aggttgttga ggaga                                                      15

<210> SEQ ID NO 29
<211> LENGTH: 5084
<212> TYPE: DNA
<213> ORGANISM: Homo sapiens

<400> SEQUENCE: 29
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga aagaagacaa cgacacgctg     420
gtccgctgtc ctctcacaga cccagaagtg accaattatt ccctcaaggg gtgccagggg     480
aagcctcttc ccaaggactt gaggtttatt cctgacccca aggcgggcat catgatcaaa     540
agtgtgaaac gcgcctacca tcggctctgt ctgcattgtt ctgtggacca ggagggcaag    600

```
tcagtgctgt cggaaaaatt catcctgaaa gtgaggccag ccttcaaagc tgtgcctgtt    660
gtgtctgtgt ccaaagcaag ctatcttctt agggaagggg aagaattcac agtgacgtgc    720
acaataaaag atgtgtctag ttctgtgtac tcaacgtgga aaagagaaaa cagtcagact    780
aaactacagg agaaatataa tagctggcat cacggtgact tcaattatga acgtcaggca    840
acgttgacta tcagttcagc gagagttaat gattctggag tgttcatgtg ttatgccaat    900
aatactttg gatcagcaaa tgtcacaaca accttggaag tagtagataa aggattcatt    960
aatatcttcc ccatgataaa cactacagta tttgtaaacg atggagaaaa tgtagatttg   1020
attgttgaat atgaagcatt ccccaaacct gaacaccagc agtggatcta tatgaacaga   1080
accttcactg ataaatggga agattatccc aagtctgaga tgaaaagtaa tatcagatac   1140
gtaagtgaac ttcatctaac gagattaaaa ggcaccgaag gaggcactta cacattccta   1200
gtgtccaatt ctgacgtcaa tgctgccata gcatttaatg tttatgtgaa tacaaaacca   1260
gaaatcctga cttacgacag gctcgtgaat ggcatgctcc aatgtgtggc agcaggattc   1320
ccagagccca caatagattg gtattttgt ccaggaactg agcagagatg ctctgcttct   1380
gtactgccag tggatgtgca gacactaaac tcatctgggc caccgtttgg aaagctagtg   1440
gttcagagtt ctatagattc tagtgcattc aagcacaatg gcacggttga atgtaaggct   1500
tacaacgatg tgggcaagac ttctgcctat tttaactttg catttaaagg taacaacaaa   1560
gagcaaatcc atccccacac cctgttcact cctttgctga ttggtttcgt aatcgtagct   1620
ggcatgatgt gcattattgt gatgattctg acctacaaat atttacagaa acccatgtat   1680
gaagtacagt ggaaggttgt tgaggagata aatggaaaca attatgttta catagaccca   1740
acacaacttc cttatgatca caaatgggag tttcccagaa acaggctgag ttttgggaaa   1800
accctgggtg ctggagcttt cgggaaggtt gttgaggcaa ctgcttatgg cttaattaag   1860
tcagatgcgg ccatgactgt cgctgtaaag atgctcaagc cgagtgccca tttgacagaa   1920
cgggaagccc tcatgtctga actcaaagtc ctgagttacc ttggtaatca catgaatatt   1980
gtgaatctac ttggagcctg caccattgga gggcccaccc tggtcattac agaatattgt   2040
tgctatggtg atcttttgaa tttttttgaga agaaaacgtg attcatttat ttgttcaaag   2100
caggaagatc atgcagaagc tgcactttat aagaatcttc tgcattcaaa ggagtcttcc   2160
tgcagcgata gtactaatga gtacatggac atgaaacctg gagtttctta tgttgtccca   2220
accaaggccg acaaaaggag atctgtgaga ataggctcat acatagaaag agatgtgact   2280
cccgccatca tggaggatga cgagttggcc ctagacttag aagacttgct gagcttttct   2340
taccaggtgg caaagggcat ggctttcctc gcctccaaga ttgtattca cagagacttg   2400
gcagccagaa atatcctcct tactcatggt cggatcacaa agatttgtga ttttggtcta   2460
gccagagaca tcaagaatga ttctaattat gtggttaaag aaacgctcg actacctgtg   2520
aagtggatgg cacctgaaag catttcaac tgtgtataca cgtttgaaag tgacgtctgg   2580
tcctatggga ttttctttg ggagctgttc tctttaggaa gcagcccta tcctggaatg   2640
ccggtcgatt ctaagttcta caagatgatc aaggaaggct tccggatgct cagccctgaa   2700
cacgcacctg ctgaaatgta tgacataatg aagacttgct gggatgcaga tcccctaaaa   2760
agaccaacat tcaagcaaat tgttcagcta attgagaagc agatttcaga gagcaccaat   2820
catatttact ccaacttagc aaactgcagc cccaaccgac agaagcccgt ggtagaccat   2880
tctgtgcgga tcaattctgt cggcagcacc gcttcctcct cccagcctct gcttgtgcac   2940
```

```
gacgatgtct gagcagaatc agtgtttggg tcacccctcc aggaatgatc tcttcttttg   3000
gcttccatga tggttatttt cttttctttc aacttgcatc caactccagg atagtgggca   3060
ccccactgca atcctgtctt tctgagcaca ctttagtggc cgatgatttt tgtcatcagc   3120
caccatccta ttgcaaaggt tccaactgta tatattccca atagcaacgt agcttctacc   3180
atgaacagaa aacattctga tttggaaaaa gagagggagg tatggactgg gggccagagt   3240
cctttccaag gcttctccaa ttctgcccaa aaatatggtt gatagtttac ctgaataaat   3300
ggtagtaatc acagttggcc ttcagaacca tccatagtag tatgatgata caagattaga   3360
agctgaaaac ctaagtcctt tatgtggaaa acagaacatc attagaacaa aggacagagt   3420
atgaacacct gggcttaaga aatctagtat ttcatgctgg aatgagaca taggccatga    3480 aaaaaatgat ccccaagtgt gaacaaaaga tgctcttctg tggaccactg catgagcttt   3540
tatactaccg acctggtttt taaatagagt ttgctattag agcattgaat tggagagaag   3600
gcctccctag ccagcacttg tatatacgca tctataaatt gtccgtgttc atacatttga   3660
ggggaaaaca ccataaggtt tcgtttctgt atacaaccct ggcattatgt ccactgtgta   3720
tagaagtaga ttaagagcca tataagtttg aaggaaacag ttaataccat tttttaagga   3780
aacaatataa ccacaaagca cagtttgaac aaaatctcct cttttagctg atgaacttat   3840
tctgtagatt ctgtggaaca agcctatcag cttcagaatg gcattgtact caatggattt   3900
gatgctgttt gacaaagtta ctgattcact gcatggctcc cacaggagtg ggaaaacact   3960
gccatcttag tttggattct tatgtagcag gaaataaagt ataggtttag cctccttcgc   4020
aggcatgtcc tggacaccgg gccagtatct atatatgtgt atgtacgttt gtatgtgtgt   4080
agacaaatat ttggaggggt atttttgccc tgagtccaag agggtccttt agtacctgaa   4140
aagtaacttg gctttcatta ttagtactgc tcttgtttct tttcacatag ctgtctagag   4200
tagcttacca gaagcttcca tagtggtgca gaggaagtgg aaggcatcag tccctatgta   4260
tttgcagttc acctgcactt aaggcactct gttatttaga ctcatcttac tgtacctgtt   4320
ccttagacct tccataatgc tactgtctca ctgaaacatt taaattttac cctttagact   4380
gtagcctgga tattattctt gtagtttacc tctttaaaaa caaacaaaa caaacaaaa     4440 aactcccctt cctcactgcc aatataaaa ggcaaatgtg tacatggcag agtttgtgtg    4500
ttgtcttgaa agattcaggt atgttgcctt tatggtttcc cccttctaca tttcttagac   4560
tacatttaga gaactgtggc cgttatctgg aagtaaccat ttgcactgga gttctatgct   4620
ctcgcacctt tccaaagtta acagattttg gggttgtgtt gtcacccaag agattgttgt   4680
ttgccatact ttgtctgaaa aattcctttg tgtttctatt gacttcaatg atagtaagaa   4740
aagtggttgt tagttataga tgtctaggta cttcaggggc acttcattga gagttttgtc   4800
ttgccatact ttgtctgaaa aattcctttg tgtttctatt gacttcaatg atagtaagaa   4860
aagtggttgt tagttataga tgtctaggta cttcaggggc acttcattga gagttttgtc   4920
aatgtctttt gaatattccc aagcccatga gtccttgaaa atattttta tatatacagt    4980 aactttatgt gtaaatacat aagcggcgta agtttaaagg atgttggtgt tccacgtgtt   5040
ttattcctgt atgttgtcca attgttgaca gttctgaaga attc                    5084
```

<210> SEQ ID NO 30
<211> LENGTH: 6633
<212> TYPE: DNA
<213> ORGANISM: Homo sapiens

<400> SEQUENCE: 30

-continued

```
ttctccccgc ccccagttg ttgtcgaagt ctgggggttg ggactggacc ccctgattgc      60
gtaagagcaa aaagcgaagg cgcaatctgg acactgggag attcggagcg cagggagttt     120
gagagaaact tttattttga agagaccaag gttgagggg gcttatttc ctgacagcta      180
tttacttaga gcaaatgatt agttttagaa ggatggacta taacattgaa tcaattacaa    240
aacgcggttt ttgagcccat tactgttgga gctacaggga gagaaacagg aggagactgc    300
aagagatcat ttgggaaggc cgtgggcacg ctctttactc catgtgtggg acattcattg    360
cggaataaca tcgaggagaa agtttcccag agctatgggg acttcccatc cggcgttcct    420
ggtcttaggc tgtcttctca cagggctgag cctaatcctc tgccagcttt cattaccctc    480
tatccttcca aatgaaaatg aaaaggttgt gcagctgaat tcatccttt ctctgagatg     540
ctttggggag agtgaagtga gctggcagta ccccatgtct gaagaagaga gctccgatgt    600
ggaaatcaga aatgaagaaa acaacagcgg ccttttgtg acggtcttgg aagtgagcag     660
tgcctcggcg gcccacacag ggttgtacac ttgctattac aaccacactc agacagaaga    720
gaatgagctt gaaggcaggc acatttacat ctatgtgcca gacccagatg tagccttgt     780
acctctagga atgacggatt atttagtcat cgtggaggat gatgattctg ccattatacc    840
ttgtcgcaca actgatcccg agactcctgt aaccttacac aacagtgagg gggtggtacc    900
tgcctcctac gacagcagac agggctttaa tgggaccttc actgtaggc cctatatctg     960
tgaggccacc gtcaaaggaa agaagttcca gaccatccca tttaatgttt atgctttaaa   1020
agcaacatca gagctggatc tagaaatgga agctcttaaa accgtgtata agtcagggga   1080
aacgattgtg gtcacctgtg ctgttttaa caatgaggtg gttgaccttc aatggactta    1140
ccctggagaa gtgaaaggca aaggcatcac aatgctggaa gaaatcaaag tcccatccat   1200
caaattggtg tacactttga cggtccccga ggccacggtg aaagacagtg agattacga    1260
atgtgctgcc cgccaggcta ccagggaggt caaagaaatg aagaaagtca ctatttctgt   1320
ccatgagaaa ggtttcattg aaatcaaacc caccttcagc cagttggaag ctgtcaacct   1380
gcatgaagtc aaacattttg ttgtagaggt gcgggcctac ccacctccca ggatatcctg   1440
gctgaaaaac aatctgactc tgattgaaaa tctcactgag atcaccactg atgtggaaaa   1500
gattcaggaa ataaggtatc gaagcaaatt aaagctgatc cgtgctaagg aagaagacag   1560
tggccattat actattgtag ctcaaaatga agatgctgtg aagagctata cttttgaact   1620
gttaactcaa gttccttcat ccattctgga cttggtcgat gatcaccatg ctcaactgg    1680
gggacagacg gtgaggtgca cagctgaagg cacgccgctt cctgatattg agtggatgat   1740
atgcaaagat attaagaaat gtaataatga aacttcctgg actatttgg ccaacaatgt    1800
ctcaaacatc atcacggaga tccactcccg agacaggagt accgtggagg gccgtgtgac   1860
tttcgccaaa gtgaggaga ccatcgccgt gcgatgcctg gctaagaatc tccttggagc    1920
tgagaaccga gagctgaagc tggtggctcc caccctgcgt tctgaactca cggtggctgc   1980
tgcagtcctg gtgctgttgg tgattgtgat catctcactt attgtcctgg ttgtcatttg   2040
gaaacagaaa ccgaggtatg aaattcgctg gagggtcatt gaatcaatca gcccggatgg   2100
acatgaatat atttatgtgg acccgatgca gctgccttat gactcaagat gggagttccc   2160
aagagatgga ctagtgcttg gtcgggtctt ggggtctgga gcgtttggga aggtggttga   2220
aggaacagcc tatggattaa gccggtccca acctgtcatg aaagttgcag tgaagatgct   2280
aaaacccacg gccagatcca gtgaaaaaca agctctcatg tctgaactga agataatgac   2340
```

```
tcacctgggg ccacatttga acattgtaaa cttgctggga gcctgcacca agtcaggccc      2400
catttacatc atcacagagt attgcttcta tggagatttg gtcaactatt tgcataagaa      2460
tagggatagc ttcctgagcc accacccaga gaagccaaag aaagagctgg atatctttgg      2520
attgaaccct gctgatgaaa gcacacggag ctatgttatt ttatcttttg aaaacaatgg      2580
tgactacatg gacatgaagc aggctgatac tacacagtat gtccccatgc tagaaaggaa      2640
agaggtttct aaatattccg acatccagag atcactctat gatcgtccag cctcatataa      2700
gaagaaatct atgttagact cagaagtcaa aaacctcctt tcagatgata actcagaagg      2760
ccttacttta ttggatttgt tgagcttcac ctatcaagtt gcccgaggaa tggagttttt      2820
ggcttcaaaa aattgtgtcc accgtgatct ggctgctcgc aacgtcctcc tggcacaagg      2880
aaaaattgtg aagatctgtg actttggcct ggccagagac atcatgcatg attcgaacta      2940
tgtgtcgaaa ggcagtacct ttctgcccgt gaagtggatg gctcctgaga gcatctttga      3000
caacctctac accacactga gtgatgtctg gtcttatggc attctgctct gggagatctt      3060
ttcccttggt ggcaccccct accccggcat gatggtggat tctacttttct acaataagat      3120 caagagtggg taccggatgg ccaagcctga ccacgctacc agtgaagtct acgagatcat      3180
ggtgaaatgc tggaacagtg agccggagaa gagaccctcc ttttaccacc tgagtgagat      3240
tgtggagaat ctgctgcctg acaatataaa aagagttat gaaaaaattc acctggactt      3300
cctgaagagt gaccatcctg ctgtggcacg catgcgtgtg gactcagaca atgcatacat      3360
tggtgtcacc tacaaaaacg aggaagacaa gctgaaggac tgggagggtg gtctggatga      3420
gcagagactg agcgctgaca gtggctacat cattcctctg cctgacattg accctgtccc      3480
tgaggaggag gacctgggca agaggaacag acacagctcg cagacctctg aagagagtgc      3540
cattgagacg ggttccagca gttccacctt catcaagaga gaggacgaga ccattgaaga      3600
catcgacatg atggacgaca tcggcataga ctcttcagac ctggtggaag acagcttcct      3660
gtaactggcg gattcgaggg gttccttcca cttctggggc cacctctgga tcccgttcag      3720
aaaaccactt tattgcaatg cggaggttga gaggaggact tggttgatgt ttaaagagaa      3780
gttcccagcc aagggcctcg gggagcgttc taaatatgaa tgaatgggat attttgaaat      3840
gaactttgtc agtgttgcct ctcgcaatgc ctcagtagca tctcagtggt gtgtgaagtt      3900
tggagataga tggataaggg aataataggc cacagaaggt gaactttgtg cttcaaggac      3960
attggtgaga gtccaacaga cacaatttat actgcgacag aacttcagca ttgtaattat      4020
gtaaataact ctaaccaagg ctgtgtttag attgtattaa ctatcttctt tggacttctg      4080
aagagaccac tcaatccatc catgtacttc cctcttgaaa cctgatgtca gctgctgttg      4140 aacttttttaa agaagtgcat gaaaaaccat ttttgaacct taaaaggtac tggtactata      4200
gcattttgct atctttttta gtgttaagag ataaagaata ataattaacc aaccttgttt      4260
aatagatttg ggtcatttag aagcctgaca actcattttc atattgtaat ctatgttat      4320 aatactacta ctgttatcag taatgctaaa tgtgtaataa tgtaacatga tttccctcca      4380
gagaaagcac aatttaaaac aatccttact aagtaggtga tgagtttgac agtttttgac      4440
atttatatta ataacatgt ttctctataa agtatggtaa tagctttagt gaattaaatt      4500
tagttgagca tagagaacaa agtaaaagta gtgttgtcca ggaagtcaga atttttaact      4560
gtactgaata ggttcccccaa tccatcgtat taaaaaacaa ttaactgccc tctgaaataa      4620
tgggattaga aacaaacaaa actcttaagt cctaaaagtt ctcaatgtag aggcataaac      4680
ctgtgctgaa cataacttct catgtatatt acccaatgga aaatataatg atcagcaaaa      4740
```

```
agactggatt tgcagaagtt ttttttttt ttcttcatgc ctgatgaaag ctttggcaac    4800
cccaatatat gtattttttg aatctatgaa cctgaaaagg gtcagaagga tgcccagaca    4860
tcagcctcct tctttcaccc cttacccccaa agagaaagag tttgaaactc gagaccataa    4920
agatattctt tagtggaggc tggatgtgca ttagcctgga tcctcagttc tcaaatgtgt    4980
gtggcagcca ggatgactag atcctgggtt tccatccttg agattctgaa gtatgaagtc    5040
tgagggaaac cagagtctgt atttttctaa actccctggc tgttctgatc ggccagtttt    5100
cggaaacact gacttaggtt tcaggaagtt gccatgggaa acaaataatt tgaactttgg    5160
aacagggttg gaattcaacc acgcaggaag cctactattt aaatccttgg cttcaggtta    5220
gtgacattta atgccatcta gctagcaatt gcgaccttaa tttaactttc cagtcttagc    5280
tgaggctgag aaagctaaag tttggttttg acaggttttc caaagtaaa gatgctactt    5340 cccactgtat gggggagatt gaactttccc cgtctcccgt cttctgcctc ccactccata    5400
ccccgccaag gaaaggcatg tacaaaaatt atgcaattca gtgttccaag tctctgtgta    5460
accagctcag tgttttggtg gaaaaaacat tttaagtttt actgataatt tgaggttaga    5520
tgggaggatg aattgtcaca tctatccaca ctgtcaaaca ggttggtgtg ggttcattgg    5580
cattctttgc aatactgctt aattgctgat accatatgaa tgaaacatgg gctgtgatta    5640
ctgcaatcac tgtgctatcg gcagatgatg ctttggaaga tgcagaagca ataataaagt    5700
acttgactac ctactggtgt aatctcaatg caagccccaa ctttcttatc caactttttc    5760
atagtaagtg cgaagactga gccagattgg ccaattaaaa acgaaaacct gactaggttc    5820
tgtagagcca attagacttg aaatacgttt gtgtttctag aatcacagct caagcattct    5880
gtttatcgct cactctccct tgtacagcct tattttgttg gtgctttgca ttttgatatt    5940
gctgtgagcc ttgcatgaca tcatgaggcc ggatgaaact tctcagtcca gcagtttcca    6000
gtcctaacaa atgctcccac ctgaatttgt atatgactgc atttgtgggt gtgtgtgtgt    6060
tttcagcaaa ttccagattt gtttccttt ggcctcctgc aaagtctcca gaagaaaatt    6120
tgccaatctt tcctactttc tatttttatg atgacaatca aagccggcct gagaaacact    6180
atttgtgact ttttaaacga ttagtgatgt ccttaaaatg tggtctgcca atctgtacaa    6240
aatggtccta tttttgtgaa gagggacata agataaaatg atgttataca tcaatatgta    6300
tatatgtatt tctatataga cttggagaat actgccaaaa catttatgac aagctgtatc    6360
actgccttcg tttatatttt tttaactgtg ataatcccca caggcacatt aactgttgca    6420
cttttgaatg tccaaaattt atatttaga aataataaaa agaaagatac ttacatgttc    6480
ccaaaacaat ggtgtggtga atgtgtgaga aaaactaact tgatagggtc taccaataca    6540
aaatgtatta cgaatgcccc tgttcatgtt tttgttttaa aacgtgtaaa tgaagatctt    6600
tatatttcaa taaatgatat ataatttaaa gtt                                6633
```

<210> SEQ ID NO 31
<211> LENGTH: 976
<212> TYPE: PRT
<213> ORGANISM: Homo sapiens

<400> SEQUENCE: 31

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

```
Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
```

-continued

```
            450                 455                 460
Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
            565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
            725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880
```

-continued

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 32
<211> LENGTH: 1089
<212> TYPE: PRT
<213> ORGANISM: Homo sapiens

<400> SEQUENCE: 32

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr

-continued

```
            275                 280                 285
Glu Cys Ala Ala Arg Gln Ala Thr Arg Glu Val Lys Glu Met Lys Lys
            290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
            325                 330                 335
Val Glu Val Arg Ala Tyr Pro Pro Arg Ile Ser Trp Leu Lys Asn
            340                 345                 350
Asn Leu Thr Leu Ile Glu Asn Leu Thr Glu Ile Thr Thr Asp Val Glu
            355                 360                 365
Lys Ile Gln Glu Ile Arg Tyr Arg Ser Lys Leu Lys Leu Ile Arg Ala
            370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
            405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
            435                 440                 445
Ile Cys Lys Asp Ile Lys Lys Cys Asn Asn Glu Thr Ser Trp Thr Ile
            450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
            485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
            515                 520                 525
Ala Ala Val Leu Val Leu Leu Val Ile Val Ile Ile Ser Leu Ile Val
            530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
            565                 570                 575
Pro Met Gln Leu Pro Tyr Asp Ser Arg Trp Glu Phe Pro Arg Asp Gly
            580                 585                 590
Leu Val Leu Gly Arg Val Leu Gly Ser Gly Ala Phe Gly Lys Val Val
            595                 600                 605
Glu Gly Thr Ala Tyr Gly Leu Ser Arg Ser Gln Pro Val Met Lys Val
            610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
            645                 650                 655
Ile Val Asn Leu Leu Gly Ala Cys Thr Lys Ser Gly Pro Ile Tyr Ile
            660                 665                 670
Ile Thr Glu Tyr Cys Phe Tyr Gly Asp Leu Val Asn Tyr Leu His Lys
            675                 680                 685
Asn Arg Asp Ser Phe Leu Ser His His Pro Glu Lys Pro Lys Lys Glu
            690                 695                 700
```

-continued

```
Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
                820                 825                 830

Lys Ile Cys Asp Phe Gly Leu Ala Arg Asp Ile Met His Asp Ser Asn
835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu

<210> SEQ ID NO 33
<211> LENGTH: 25
<212> TYPE: DNA
```

```
<213> ORGANISM: Artificial Sequence
<220> FEATURE:
<223> OTHER INFORMATION: Description of Artificial Sequence:  Synthetic
      Primer

<400> SEQUENCE: 33
ccttggtaat cacatgaata ttgcg                                            25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 34
ccttggtaat cacatgaata ttgtg                                            25

<210> SEQ ID NO 35
<211> LENGTH: 420
<212> TYPE: DNA
<213> ORGANISM: Homo sapiens

<400> SEQUENCE: 35
aactgcttat ggcttaatta agtcagatgc ggccatgact gtcgctgtaa agatgctcaa      60
gcgtaagttc ctgtatggta ctgcatgcgc ttgacatcag tttgccagtt gtgcttttttg    120 ctaaaatgca tgtttccaat tttagcgagt gcccatttga cagaacggga agccctcatg    180
tctgaactca aagtcctgag ttaccttggt aatcacatga atattgtgaa tctacttgga    240
gcctgcacca ttggaggtaa agccgtgtcc aagctgcctt ttattgtctg tcaggttatc    300
aaaacatgac attttaatat gattttggca atgctagatt ataaactgct tggaagattt    360
ttttacccag actgttgttc tctcttgcta gattttgttt tcctcattgt tcttaagaat    420

<210> SEQ ID NO 36
<211> LENGTH: 420
<212> TYPE: DNA
<213> ORGANISM: Homo sapiens

<400> SEQUENCE: 36
aactgcttat ggcttaatta agtcagatgc ggccatgact gtcgctgtaa agatgctcaa      60
gcgtaagttc ctgtatggta ctgcatgcgc ttgacatcag tttgccagtt gtgcttttttg    120 ctaaaatgca tgtttccaat tttagcgagt gcccatttga cagaacggga agccctcatg    180
tctgaactca aagtcctgag ttaccttggt aatcacatga atattgcgaa tctacttgga    240
gcctgcacca ttggaggtaa agccgtgtcc aagctgcctt ttattgtctg tcaggttatc    300
aaaacatgac attttaatat gattttggca atgctagatt ataaactgct tggaagattt    360
ttttacccag actgttgttc tctcttgcta gattttgttt tcctcattgt tcttaagaat    420
```

MUTATIONS IN KIT CONFER IMATINIB RESISTANCE IN GASTROINTESTINAL STROMAL TUMORS

The present invention claims priority to U.S. Provisional Patent Application Ser. No. 60/578,403, filed on Jun. 9, 2004, which is incorporated by reference herein in its entirety.

STATEMENT REGARDING FEDERALLY SPONSORED RESEARCH OR DEVELOPMENT

The generation of the present invention utilized federal funds pursuant at least to National Cancer Institute Grant No. 5 P30 CA016672 28. The United States Government has certain rights in the invention.

FIELD OF THE INVENTION

The present invention relates to the fields of cell biology, molecular biology, and cancer diagnosis and therapy. In particular, the invention regards mutations in KIT that confer drug resistance to cancer.

BACKGROUND OF THE INVENTION

Chemotherapeutic agents are an effective means to treat cancer, particularly when the agent is well-suited to target the specific direct or indirect molecular origin of the disease. However, in some cases, resistance to one or more chemotherapeutic agents manifests during treatment, and sometimes a particular agent becomes wholly ineffective in certain individuals. In some embodiments, this resistance may derive from mutations that arise in a particular gene directly or indirectly associated with the cancer. Although resistance to chemotherapeutic agents has occurred in a wide variety of cancers, the present invention, in particular embodiments, regards resistance to chemotherapeutic agents that provide therapy for gastrointestinal stromal tumors (GISTs).

GISTs originate from transformation of interstitial cells of Cajal, a network of innervated cells that coordinate peristalsis in the gastrointestinal system. Aberrant KIT signal represent the initiating event in the pathogenesis of GISTs and KIT gain of function mutations have been reported (Hirota et al., 1998; Lux et al., 2000; Lasota et al., 2000; Corless et al., 2002; Rubin et al., 2001; Sandberg and Bridge, 2002; Heinrich et al., 2002; Koh et al., 2004). Microarray analysis showed that GISTs exhibit a remarkably homogeneous gene expression profile unlike the extremely heterogeneous patterns seen in common epithelial cancers (Allander et al., 2001). KIT with an exon 11 mutation that replaced Lys558 with Val (Lys558Val) was introduced by knock-in strategy, and that produced tumors indistinguishable from human GISTs (Sommer et al., 2003). These results indicate that constitutive KIT signaling is both critical and sufficient for GIST.

The locations of KIT mutations are nonrandom and vary according to cell lineage. KIT exon 11 is the most frequent mutation site for GISTs (Hirota et al., 1998; Lux et al. 2000; Lasota et al., 2000; Corless et al., 2002; Rubin et al., 2001), most commonly clustered in the cytoplasmic juxtamembrane region between 550 and 563, resulting in pathological release from autoinhibition (Ma et al., 1999; Chan et al., 2003) and constitutive activation of KIT. Mutations in exon 9 make up 3% to 21% of all cases (Lasota et al., 2000; Rubin et al., 2001; Hirota et al., 2001). Mutation in exon 13 is rare; to date there are only five reported cases (Lux et al., 2000; Lasota et al., 2000; Sakurai et al., 2001; Kinoshita et al., 2003), all exhibiting the same 1945A→G, Glu642Lys mutation which is 12 amino acids N-terminal to a novel mutation provided herein. Exon 17 mutation is extremely rare in GISTs with only three reported cases so far, two sporadic cases with Asn822His and Asn822Lys (Heinrich et al., 2003) and one Asp820Tyr mutation in a patient with familial GIST with dysphagia (Hirota et al., 2002). GISTs with wild type KIT (Rubin et al., 2001; Heinrich et al., 2003; Hirota et al., 2003) range from 8-35% of cases and often have PDGFR α activating mutation (Heinrich et al., 2003; Hirota et al. 2003). Imatinib (also referred to as imatinib mesylate, gleevec, glivec, or STI571) (Fabbro et al., 2002; Manley et al., 2002) is a selective ATP-competitive inhibitor of KIT, BCR-ABL, and PDGFRα and β and is the only drug effective against GISTs (Demetri et al., 2002; Kitamura et al., 2003; Heinrich et al., 2003; Joensuu et al., 2001; Dei Tos, 2003; van Oosterom et al., 2001). Imatinib revolutionized the care of GIST patients and represents a new paradigm of targeted cancer chemotherapy. Unfortunately, imatinib resistance has begun to emerge. Elucidation of one or more drug resistance mechanisms, especially, for an extremely effective selective tyrosine kinase inhibitor like imatinib should provide new insights in reversing drug resistance and identifying new targets for cancer therapy.

Tuveson et al. (2001) describe a homozygous exon 13 missense mutation in c-KIT at K642E utilized to establish a human GIST cell line. Although the KIT protein was constitutively tyrosine phosphorylated, this phosphorylation was abolished after introducing STI571 to the cells.

US 2004/0005623 regards assessment of whether a specific drug that can inhibit one form of a tumor expressing activated KIT protein can also interact with and treat other tumors. In particular embodiments, the interaction between a drug and enzyme from a patient tumor is determined through analysis of nucleotide sequence of at least part of a c-KIT allele.

BRIEF SUMMARY OF THE INVENTION

The present invention is directed to a system and method that relate to mutation-mediated resistance to chemotherapeutic treatment for cancer. In particular aspects, the frequency of a novel mutation in pre-imatinib gastrointestinal stromal tumors (GIST) provides prognostic information. In further aspects, the frequency allows prediction of response duration (or progression-free survival) to imatinib and helps health care providers to choose an appropriate targeted therapy (or therapies), such as an individualized therapy.

Detection of mutations associated with resistance to therapy for GIST may occur by any suitable method in the art. In particular aspects, the detection of one or more mutations occurs via a method that facilitates determination of frequency of the mutation, such as small pool polymerase chain reaction, for example. Small pool-PCR (SP-PCR) may be employed to determine the frequency of mutations that are capable of conferring drug resistance. In specific embodiments, the pre-existing frequency of mutation is utilized as a prognostic measure. In further specific embodiments, the pre-existing frequency of mutation is employed for treatment decision, such as using an individualized therapy, to assist health care providers in selecting the most effective drug as a therapy, which may be considered a front-line therapy, among several targeted drugs, such as several equally effective targeted drugs.

In a particular aspect of the invention, the mutation that confers resistance is in a tyrosine kinase, such as in the drug binding pocket, ATP-binding domain, and/or kinase domain of KIT, ABL, or PDGFRA. In a specific aspect of the invention, the cancer for which there is resistance to the drug comprises an aberrant KIT signal, such as aberrant KIT sequence or expression. In further embodiments, the cancer is initially responsive to drug therapy, such as chemotherapy. In particular, the present invention regards mutations that confer resistance to a chemotherapeutic treatment for GISTs, such as imatinib, although any cancer in which KIT is directly or indirectly related and is responsive to a chemotherapeutic agent, such as imatinib, is within the scope of the invention. The aberrant KIT signal may be a contributor or cause of the cancer, and in specific embodiments there may be detectable c-KIT expression; a KIT polynucleotide may be mutated (for example, such that it encodes a constitutively active KIT gene product); the expression level of KIT may be altered, such as with overexpression; or a combination thereof. Other than GISTs, ovarian cancer may comprise c-KIT expression and show resistance to imatinib (Raspollini et al., 2004). Cancers that comprise c-KIT expression are within the scope of the invention.

KIT gain of function mutations play an important role in the pathogenesis of gastrointestinal stromal tumors (GISTs). Imatinib is a selective tyrosine kinase inhibitor of at least ABL, PDGFR and KIT and represents a new paradigm of targeted therapy against GISTs. Here, the present inventors demonstrate that following imatinib treatment, an additional specific and novel KIT mutation occurs in GISTs as they develop resistance to the drug. Twelve GIST patients with initial near complete response to imatinib were characterized. Seven harbored mutations in KIT exon 11 and 5 harbored mutations in exon 9. Within 31 months, 6 imatinib-resistant rapidly progressive peritoneal implants (metastatic foci) developed in 5 patients. Quiescent residual GISTs persisted in 7 patients. All 6 rapidly progressive imatinib-resistant implants from 5 patients show an identical novel KIT missense mutation, 1982T→C, that resulted in Val654Ala in KIT tyrosine kinase domain 1. This novel mutation may not be detectable by conventional PCR, such as nested PCR, in pre-imatinib or post-imatinib residual quiescent GISTs and is strongly correlated with imatinib resistance, particularly given that these clones were isolated from the in vivo state in the patients. However, in some embodiments a mutation may be undetectable in a pre-imatinib sample, which would indicate that the mutation was not present or that it was present in a low enough frequency to escape detection by conventional and current polymerase chain reaction methods. In this case, mutation-specific polymerase chain reaction may be utilized to detect the mutation. In a specific embodiment, this is achieved through small pool polymerase chain reaction. A skilled artisan recognizes that detection of the frequency of the mutation, such as by small pool polymerase chain reaction, and its correlation to the duration of remission may be prognostic for the disease treatment.

Thus, in specific embodiments the present invention provides one or more mutations in KIT that are associated with resistance to imatinib or a related drug, such as a mutation that allows a similar altered allosteric configuration to the KIT polypeptide such that it is no longer an effective target for the drug. Other drugs with similar allosteric configurations as imatinib would also be affected by the corresponding KIT resistance-conferring mutation(s) and are also within the scope of the invention.

Thus, in some embodiments of the invention, there is a mutation that is evaluated or identified, such as one that is associated with an increased risk for developing resistance to, for example, imatinib or one that is associated with developing resistance to, for example, imatinib. As a result of the evaluation for and upon identification of the resistance-conferring mutation, the therapy is adjusted to circumvent at least some therapy resistance issues. For example, an alternative anticancer therapy is employed, such as an alternative chemotherapeutic, and/or a change in imatinib dosage is employed, including a higher dosage of the drug. In further specific embodiments, the absence or presence of this mutation and/or the frequency of this mutation in GISTs at the time of diagnosis can predict imatinib response, duration of response, and/or prognosis, and facilitate selection of one or more treatment regimens, such as treatment with one or more other anticancer treatments, including targeting one or more tyrosine kinase inhibitors. In one aspect of the invention, the KIT mutation, such as the exemplary missense 1982T→C (Val654Ala), is further defined as a tumor marker for GISTs.

The mutation that confers resistance to a particular therapy, such as imatinib, may be present prior to or subsequent to the onset of cancer or prior to or subsequent to the onset of the therapy. In specific embodiments, the mutation that confers drug resistance is pre-existing at very low frequency prior to treatment. Under the selection pressure of drug treatment, the mutated clone outgrows other cells and results in drug resistance and rapid progression. In particular aspects of the invention, there is correlative analysis of the pre-existing mutation that confers resistance with clinical duration of response. For example, the frequency of pre-existing mutation(s) prior to treatment can serve as a tumor marker for prognosis and treament decision-making.

Thus, in some embodiments of the present invention, an assessment can be made about the risk of developing resistance to imatinib based on the genotype of the individual. In particular embodiments, the genotype of the KIT locus is identified, and the resistance-conferring mutation may be present at any region of the locus such that it confers resistance to imatinib. That is, the term "gene" refers to coding (exons) and noncoding regions for KIT, such as intronic regions, 3' untranslated regions, 5' untranslated regions, and upstream promoter regions, for example. In a particular embodiment, the resistance-conferring mutation is present in the coding region, and in further embodiments the mutation is in a coding region encoding an ATP-binding domain, a drug-binding domain, or kinase domain of KIT. In particular embodiments, more than one mutation may be necessary to produce resistance, in addition to any one or more mutations associated with the original development of GIST. The genotype may be determined from a sample provided by an individual suspected of being able to develop resistance to imatinib, by an individual diagnosed with GIST yet prior to receiving treatment, or by an individual that has already developed resistance to imatinib, for example. The sample may comprise a cell and may be of any suitable kind, such as blood, urine, or any other bodily fluid, or a tissue sample or cell culture, for example.

Correlation between genotype and phenotype is one of the hallmarks of pharmacogenetics. Identification between a mutation and the phenotype that it confers is useful information, as it allows for screening of a patient's genotype to yield significant information about the patient's phenotype. The present invention includes methods for identifying a mutation in KIT that confers resistance to imatinib by obtaining a sample from an individual with cancer and evaluating a KIT polynucleotide in the sample for one or more mutations. The mutation may be identified as being resistant to imatinib by any suitable means in the art, but certainly a recurrence of the cancer, or reversal of any beneficial effects seen initially with the imatinib therapy, are some examples that comprise identifying a resistance-conferring mutation. At a molecular level, identifying a correlation between genotype and phenotype may be employed and require a number of data points to be evaluated. With respect to imatinib-resistance phenotype, either the KIT polynucleotide or polypeptide may be evaluated. Some of the embodiments of the invention involve comparing the KIT genotype in a patient against a KIT genotype in a population of individuals.

Thus, development of resistance to imatinib may be detected by any means suitable in the art. The resistance-conferring mutation may be identified in a polynucleotide comprising the mutation or in a polypeptide encoded by the defective polynucleotide. In the particular embodiment concerning the 1982T→C mutation, it may be detected in a KIT polynucleotide, such as by sequencing, polymerase chain reaction, in situ hybridization, or a combination thereof, for example, or it may be detected as the corresponding encoded form (Val654Ala) in a KIT polypeptide, such as by immunohistochemistry or 2-D gel electrophoresis, for example.

In some embodiments, the nucleotide sequence of base 1982 in one or both alleles of KIT is determined. The absence of a thymidine at this position correlates with a propensity for imatinib resistance. In lieu of thymidine at base 1982, there may be an adenine, guanine, or cytosine. In specific embodiments, there is a cytosine at base 1982 that confers imatinib resistance. Thus, in accordance with particular aspects of the invention, there is an isolated KIT polynucleotide comprising a mutation at 1982T, such as one further defined as being a 1982T→C mutation. This isolated polynucleotide may be comprised alone or it may be comprised on a vector, such as a viral vector or a non-viral vector. The viral vector may be, for example an adenoviral vector, a retroviral vector, a rheovirus vector, or an adeno-associated vector. In embodiments wherein the vector is a non-viral vector, one example includes a plasmid. In another aspect of the invention, the polynucleotide is further defined as being comprised in a suitable container, and including one or more of the following: deoxynucleotide triphosphates; one or more primers; polymerase; and buffer.

In other aspects of the invention, the isolated polynucleotide is further defined as being associated with a substrate, such as, for example, a microchip. The isolated polynucleotide may alternatively be comprised in a cell, such as in an isolated cell, a cell suspension, a cell line, or in a mammal, for example. The mammal may be a human, and the cell may be cancerous.

In a particular aspect of the invention, there is a method of determining therapy for an individual with cancer, wherein the cancer is characterized by having at least one cell comprising a KIT polynucleotide, such as a KIT polynucleotide comprising a gain of function mutation, wherein the method comprises providing a sample from the individual; assaying the sample for a 1982T mutation in a KIT polynucleotide; and providing therapy to the individual based on the assay. The cancer may comprise gastroinstestinal stromal tumor (GIST) or ovarian cancer, for example, In specific embodiments, the cancer comprises GIST.

Samples from individuals may be of any kind, such that they provide suitable substrates for analysis for resistance to imatinib therapy, such as polynucleotides, which may be DNA or RNA, for example, or polypeptides. The sample may be comprised in paraffin or may be frozen, for example. In particular embodiments, the sample from the individual comprises a fluid, a cell, a tissue, or a combination thereof. The sample may comprise blood, urine, saliva, sweat, feces, or nipple aspirate, for example.

For embodiments wherein KIT polynucleotides are assayed for presence and frequency of resistance-conferring mutations, the assaying step may comprise any suitable means. For example polymerase chain reaction, such as small pool polymerase chain reaction, may be employed. The polymerase chain reaction may utilize a primer that comprises the mutation, such as a primer comprising SEQ ID NO:26. In specific embodiments, the polymerase chain reaction proceeds only if one of the primers is extendible by polymerization, such as would be the case, for example, if the complementary nucleotide(s) to the mutant nucleotide(s) in question was at the very 3' end of the primer. Hybridization (and subsequent polymerization) would only occur if the mutation was present in the target sense polynucleotide. Alternatively, the primer may comprise the mutant polynucleotide(s) at the very 3' end of the primer, and hybridization and polymerization would only occur if the complement to the mutant polynucleotide(s) was present in the target antisense polynucleotide. In the embodiment wherein small pool polymerase chain reaction is employed, a skilled recognizes that a minute amount of starting material may be utilized, such as an amount as low as one molecule of nucleic acid, and that in this embodiment the conditions for the reaction must be suitable. For example, special precautions may be taken to decrease the risk for contamination, such as by occurring in an isolated location and/or by utilizing special equipment, including uv-irradiated equipment, and/or a hood.

In one aspect of the invention, there is a method for evaluating therapy for an individual with gastrointestinal stromal tumor (GIST), comprising providing a sample from the individual; assaying the sample for a mutation in KIT that confers resistance to a therapy for the GIST; and determining the therapy for the individual based on the presence or absence of the mutation. The mutation that confers resistance may be anywhere in the KIT polynucleotide, although in particular embodiments it is in a region that encodes, at least in part, an ATP-binding domain, a drug binding domain, or a kinase domain. The exemplary mutation in KIT is at nucleotide 1982T, in specific embodiments, and may comprise 1982T→C, in particular. The method to assay for mutation may occur prior to imatinib therapy or concomitant with imatinib therapy. In specific embodiments of the method, the method further includes the step of providing the therapy to the individual. When the mutation is determined to be present in the KIT polynucleotide, the therapy of choice for the individual is preferably alternative to imatinib.

In an additional aspect of the invention, there is a method of screening an individual for imatinib resistance comprising identifying an individual in need of screening for imatinib resistance and identifying one or more nucleotides in a KIT polynucleotide that correlates with the imatinib resistance. The individual may have GIST, and the nucleotide may be at 1982 of a KIT polynucleotide, for example. In a particular embodiment, the identifying of the nucleotide step is further defined as providing a sample from the individual and assaying it by polymerase chain reaction.

The invention also includes a method of prescribing a therapy for a cancer correlating with a mutated KIT polynucleotide and being at least initially responsive to the therapy by obtaining a sample from an individual having at least one cancer cell that comprises a defective KIT polynucleotide, wherein the individual is in need of cancer therapy, and assaying for the presence or absence of a mutation in the mutated KIT polynucleotide.

At least some compositions of the invention include a polynucleotide comprising SEQ ID NO:26. Also provided is a kit for identifying a mutation in a KIT polynucleotide in a subject, comprising in a suitable container at least one of the following exemplary polynucleotides: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:26, or SEQ ID NO:27, for example. In addition, there is a KIT primer comprising sequence that is indicative of conferring resistance to imatinib, such as wherein the sequence that is indicative of conferring resistance to imatinib comprises one particular nucleotide. The particular nucleotide may be the very last nucleotide at the 3' end of the primer.

In an additional aspect of the invention, there is a method of determining a predisposition to imatinib resistance in an individual, by providing a sample from the individual, wherein the sample comprises a KIT polynucleotide, and identifying the predisposition by utilizing a primer that detects a sequence indicative of the imatinib resistance. The identifying step may be further defined as subjecting the primer to suitable polymerization conditions, such that when polymerization from the primer occurs, the sequence indicative of imatinib resistance is present in the KIT polynucleotide. In specific embodiments, the individual has GIST. The method may occur prior to or concomitant with imatinib therapy. Furthermore, when the sequence is identified in the individual, it preferably provides prognosis and/or treatment information.

In particular embodiments of the invention, mutations within the scope of the invention also confer resistance to other agents, such as other chemotherapeutic agents. For example, the mutation may affect binding of agents that comprise a similar allosteric conformation to imatinib. A skilled artisan recognizes that there are means to compare allosteric conformation between imatinib and the agent in question, such as by comparing crystal structures and/or by comparing computer-generated models of the two agents, for example.

In particular aspects of the invention, a PDGFRA polynucleotide comprises a resistance-conferring mutation, and methods and compositions analogous to those provided for KIT are also within the scope of the invention.

In one aspect of the invention, there is an isolated human KIT polynucleotide comprising a mutation at 1982T. The mutation may be any mutation, although in particular embodiments it is a 1982T→C mutation. The polynucleotide may be comprised in a vector, such as a viral vector, for example an adenoviral vector, a retroviral vector, an adeno-associated vector, or a rheoviral vector, or it may be comprised in a non-viral vector, such as a plasmid. The polynucleotide may be comprised in a suitable container, said container including one or more of the following deoxynucleotide triphosphates; one or more primers; polymerase; and buffer. In specific embodiments a polynucleotide is associated with a substrate, such as a microchip, or it may be comprised in a cell, including in a cell line or in a mammal, such as a human. In particular embodiments, the cell is cancerous.

In another aspect of the invention, there is a method of determining therapy for an individual with cancer that is characterized by having at least one cell comprising an aberrant KIT sequence or expression and that is initially responsive to a drug, comprising providing a sample from the individual; assaying the sample for at least one drug resistance-conferring mutation in a KIT polynucleotide; and providing therapy to the individual based on the assay. The aberrant KIT sequence or expression may comprise a gain of function mutation in KIT. The drug resistance-conferring mutation may be in a region of the KIT polynucleotide that encodes an ATP-binding domain, a drug-binding region, or a kinase domain. In particular, the drug resistance-conferring mutation may be at 1982T in the KIT polynucleotide. In specific embodiments, the cancer comprises gastrointestinal stromal tumor (GIST) or ovarian cancer.

Samples derived from individuals for analysis may be comprised in paraffin or may be frozen, and the sample from the individual may comprise fluid, cell, tissue, or a combination thereof. In a particular aspect of the invention, assaying step comprises polymerase chain reaction.

In another aspect of the invention, there is a method for evaluating therapy for an individual with gastrointestinal stromal tumor (GIST), comprising providing a sample from the individual; assaying the sample for a mutation in KIT that confers resistance to a therapy for the GIST; and determining the therapy for the individual based on the presence or absence of the mutation, which may be in a region of KIT that encodes an ATP-binding domain, a drug binding domain or a kinase domain. In a specific embodiment, the mutation in KIT is at nucleotide 1982T, and may be further defined as comprising 1982T→C. Wherein polymerase chain reaction is utilized, a primer that comprises the mutation or the complement thereof may be used, such as SEQ ID NO:26. The determining step for the method may occur prior to imatinib therapy or concomitant with imatinib therapy. In some embodiments, the method further comprises the step of providing the therapy to the individual. When the mutation is determined to be present in the KIT polynucleotide, the therapy for the individual may be alternative to imatinib therapy.

In an additional aspect of the invention, there is a method of screening an individual for imatinib resistance comprising identifying an individual in need of screening for imatinib resistance; and identifying one or more nucleotides in a KIT polynucleotide that correlates with the imatinib resistance. The identifying of the nucleotide step may be further defined as providing a sample from the individual; and assaying the sample by polymerase chain reaction, such as with small-pool polymerase chain reaction. The polymerase chain reaction may utilize a primer comprising the mutation or a complement thereof, such as a primer comprising SEQ ID NO:26.

In another aspect of the invention, there is a method of prescribing a therapy for a cancer correlating with a KIT polynucleotide comprising a gain of function mutation, comprising obtaining a sample from an individual having the cancer and having at least one cancer cell that comprises a drug resistance-conferring mutation; and assaying for the presence or absence of a drug resistance-conferring mutation in the KIT polynucleotide. The mutation may be in a region of the polynucleotide that encodes an ATP-binding domain, a drug binding domain, or a kinase domain.

Other embodiments of the invention include a polynucleotide comprising SEQ ID NO:26. Kits are also within the scope of the invention, such as for identifying a drug resistance-conferring mutation, wherein the kit is in a suitable container and comprises at least one of the following: a wild-type KIT polynucleotide; at least one KIT polynucleotide comprising a drug resistance-conferring mutation; or a primer that identifies the resistance-conferring mutation.

A specific kit for identifying a mutation in a KIT polynucleotide in a subject, may comprise in a suitable container at least one of the following exemplary polynucleotides: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:26, or SEQ ID NO:27.

In an additional aspect of the invention, there is a method of determining a predisposition to imatinib resistance in an individual, comprising providing a sample from the individual, wherein the sample comprises a KIT polynucleotide; and identifying the predisposition by utilizing a primer that detects a sequence indicative of said imatinib resistance. The identifying step may be further defined as subjecting the primer to suitable polymerization conditions, such that when polymerization from the primer occurs, the sequence indicative of imatinib resistance is present in the KIT polynucleotide. In specific embodiments, the individual has GIST. The method may occur prior to imatinib therapy. In specific embodiments, when the sequence is identified in the individual, it provides prognosis and/or treatment information.

In specific aspects of the invention, there is a KIT primer, comprising sequence that is indicative of conferring resistance to imatinib. The sequence that is indicative of conferring resistance to imatinib may comprise one or more particular nucleotides. In specific embodiments, the particular nucleotide is at the 3' end of the primer. The particular nucleotide may represent a mutation in a KIT polynucleotide that confers resistance to imatinib, or the complement thereof. In a specific embodiment, the primer comprises SEQ ID NO:26.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A-1D show CT, positron emission tomography (PET) and PET CT scan images of patient A (a-1-10), patient B (b-1-4), patient C (c-1-4) and patient D (d-1-4), respectively.

In FIG. 4A, there is agarose gel electrophoresis. Four bands were visualized as indicated. In FIG. 4B, there is a chromatogram of allelic-specific sequencing data. Top left panel, the 579 bp DNA show exon 11 wild type sequence containing the BseRI recognition site, GAGGAG. Top right panel, the 454 bp DNA show the wild type 1982T. Lower panel, the 564 bp DNA, which is the undigested original mutated allele contain the 2nd 1982 T→C mutation.

In FIG. 6A, there is a crystal structure of wild type KIT in complex with imatinib (center structure having rings) showing activation loop (bottom right quadrant), the two important amino acids R796 and D792, and the location of the 3 reported second mutations in KIT that confer imatinib resistance, V654, T670 and Y823. The 3D structure of mutated KIT, V654A, T670I, and Y823D are shown in FIGS. 6B, 6C, and 6D, respectively.

FIG. 7 shows mutation-specific and wild-type KIT primer sequences. Portions of introns 12 and 13 of the human KIT gene are typed in lower case, and exon 13 is typed in upper case. The inner primers (or nested primers) are chosen from exon 13 and are shown in uppercase in the middle box. The outer forward and outer reverse primers are chosen from intron 12 and intron 13, respectively, and are shown in lowercase within boxes with grey highlight. Mutation-specific Forward Inner is designated as "Mutation FI" and the sequence comprised the following: 5'-CCT TGG TAA TCA CAT GAA TAT TG<u>C</u> G (SEQ ID NO:33); Wild type Forward Inner is designated as "Wild type-FI" and the sequence comprised the following: 5'-CCT TGG TAA TCA CAT GAA TAT TG<u>T</u> G (SEQ ID NO:34). Forward Outer primer is designated as the following: "FO" and the sequence comprised the following: 5'-TAC TGC ATG CGC TTG ACA TC (SEQ ID NO:6); Reverse Inner/Outer primer is designated as "RIO" and the sequence comprised the following: 5'-CCA AGC AGT TTA TAA TCT AGC (SEQ ID NO:27). The entire sequence in the figure having the "T" nucleotide is provided in SEQ ID NO:35, whereas the entire sequence in the figure having the "C" nucleotide is provided in SEQ ID NO:36.

DETAILED DESCRIPTION OF THE INVENTION

I. Definitions

Figure 1A:
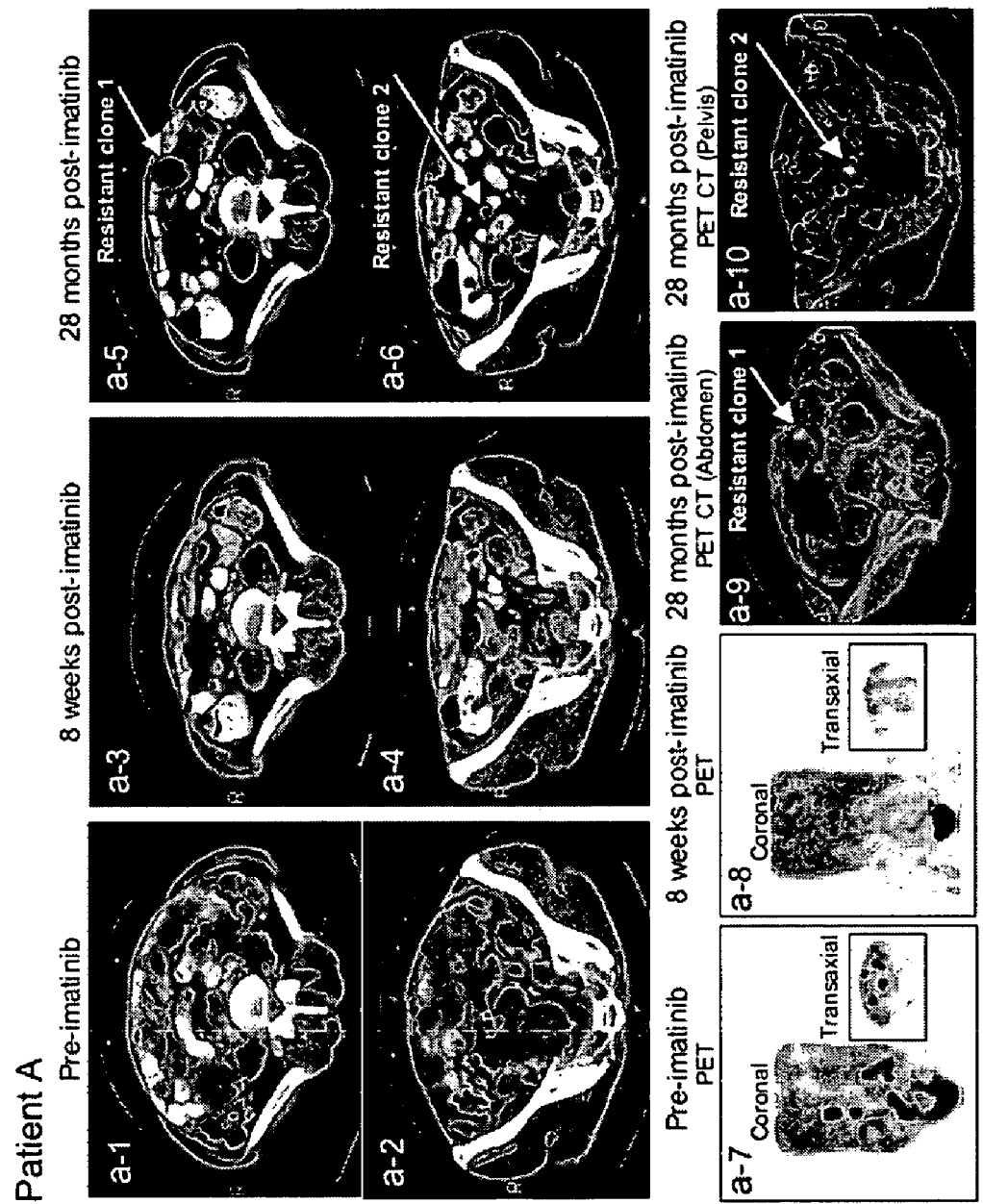

As used herein the specification, "a" or "an" may mean one or more. As used herein in the claim(s), when used in conjunction with the word "comprising", the words "a" or "an" may mean one or more than one. As used herein "another" may mean at least a second or more.

The term "gastrointestinal stromal tumor (GIST)" as used herein refers to tumors located in the gastrointestinal tract (such as the stomach, the small intestine, and the large intestine) or in surrounding organs or tissues (such as the appendix, ampulla vater, rectum, omentum, anus, or the esophagus). In specific embodiments, the tumors comprise at least one cell expressing c-KIT or comprising a gain of function mutation in KIT, and in further specific embodiments the cell comprises a drug resistance-conferring mutation that arises before or during therapy. In specific embodiments, the tumor arises from at least one intersitial cell of Cajal (ICC) or one or more precursors or pluripotential stem cells thereof. In additional embodiments, the cell also expresses other markers, such as CD34, SMA, desmin, S-100, or any combination thereof.

II. The Present Invention

The present invention regards the development of resistance to chemotherapeutic therapy for cancer, particularly in cancers having aberrant tyrosine kinase expression, such as a mutated or overexpressed tyrosine kinase, and has become resistant to one or more chemotherapeutic agents. In specific embodiments, the invention regards development of resistance to a drug that targets a particular tyrosine kinase, such as KIT, ABL, or PDGFRA. In specific embodiments, the invention concerns resistance to imatinib therapy through one or more mutations in a KIT polynucleotide, such as with GISTs.

GIST patients often present with liver metastases and peritoneal implants. Each individual peritoneal implant can be viewed as a single clone growing in vivo, which can be monitored clinically by CT scan and PET scan, for example, and intervention by surgery or biopsy can be performed at the onset of radiographic progression, for example. Each clinical phase of disease and tumor evolution can be correlated with specific molecular events, in some embodiments of the invention. Taking advantage of the unique features of GISTs, the present invention provides a novel KIT mutation in exon 13 that correlates with emergence of imatinib resistance and rapid progression in GISTs. For example, there is a novel KIT missense mutation, 1982T→C, that resulted in Val654Ala in KIT tyrosine kinase domain 1. For reference, this mutation is at nucleotide 1982 in SEQ ID NO:29, and by comparison to other KIT polynucletoides the corresponding nucleotide can be identified. This novel mutation is not present in pre-imatinib or post-imatinib residual quiescent GISTs and is strongly correlated with imatinib resistance. Allelic-specific sequencing data show that this new mutation occurs in the allele harboring original activation mutation of KIT. In specific embodiments, a mutation is not detectable in pre-imatinib or post-imatinib residual quiescent GISTs by standard PCR but is detectable by more sensitive methods, such as small pool PCR, such as due to its low frequency.

Therefore, the present invention provides for a cancer having aberrant KIT sequence or expression, such as a mutation in KIT, for example a gain of function mutation in KIT, that correlates indirectly or directly with the cause of the disease itself and that subsequently (or even originally) exhibits a separate mutation that confers resistance to the drug for the cancer. The invention concerns the identification of this additional resistance-conferring mutation and subsequent alteration in therapy to contitnute to provide effective cancer treatment for the individual in need of the therapy.

III. Gastrointestinal Stromal Tumors

The exemplary embodiment of cancer that develops resistance-conferring mutations in KIT and diagnosis thereof comprises GISTs, which are the most common mesenchymal tumors in the intestinal tract. Although they typically arise in the gastrointestinal tract, including the stomach, small intestine, and large intestine, they may also occur in the appendix, ampulla vater, rectum, omentum, anus, and, perhaps, the esophagus. Given that the omentum, for example, does not arise from the interstitial cells of Cajal (ICC), this suggests that a precursor or pluripotential stem cell that can give rise to the ICC may be the primary cell of GISTs.

Microarray analysis has shown that GISTs exhibit a remarkably homogenous gene expression profile unlike the extremely heterogeneous patterns seen in, for example, epithelial cancers. GISTs are usually characterized by the expression of KIT, which may also be referred to as CD117. Although a small percent of GISTs comprise PDGFRA mutation and wild-type KIT, in many GISTs the KIT gene is mutated, resulting in consitutive activation of the protein and aberrant growth, in some embodiments. GISTs are also characterized as having spingle, epithelioid, or mixed histology. They can be identified, in some aspects of the invention, by immunohistochemical staining for KIT (CD117), which tends to impart strong diffuse cytoplasmic staining in the vast majority of tumor cells. However, in some embodiments the tumor cells also express CD34 and SMA and, to a smaller extent, desmin and S-100.

The majority of KIT mutations associated with GISTs are located in exon 11, which encodes the juxtamembrane domain, although other mutations reside in exon 17, which encodes the second catalytic domain; exon 13, which encodes the first catalytic domain; and exon 9, which encodes the most distal portion of the extracellular domain.

KIT, therefore, is an ideal target for therapy of GISTs. The development of imatinib mesylate, which is also referred to as Gleevec (Novartis, East Hanover, N.J.), STIb 1571 or CPG 57148B, provides effective therapy of GISTs directed toward KIT as a target. Imatinib is a phenylaminopyrimidine that was originally identified in vitro to inhibit the kinase activity of some members of the tyrosine kinase subclass III family, such as KIT and PDGFRA. In particular embodiments, imatinib is safe with acceptable side effects in doses up to about 800 mg. Following phase II studies, it became clear that resistance to imatinib was a factor, and the mechanisms for acquiring such resistance, in some embodiments, arises from new mutations in KIT, resulting in target resistance.

IV. Alternative Therapies Following Imatinib Resistance with Inventive Mutations In the present invention, the 1982T→C KIT mutation or other similar mutations identifies an imatinib-resistant cancer cell. The identification of this particular mutation in an individual with cancer provides an advantage for altering cancer therapies to circumvent or overcome imatinib resistance. The characteristic 1982T→C KIT mutation may be identified prior to or during imatinib therapy. In specific aspects of the invention, upon identification of this mutation the health care provider will adjust the therapy, such as by providing an alternative therapy in addition to or in lieu of imatinib, to ensure continued effective treatment for the individual.

Any alternative therapies to KIT-mediated cancers that are effective against the cancer cells having this mutation for imatinib resistance, such as GIST cancer cells having this mutation, are encompassed within the scope of the invention. The alternative therapy may be another chemotherapeutic agent, radiation, surgery, immunotherapy, gene therapy, hormone therapy, or a combination thereof, for example. In some aspects, the dosage of imatinib may be increased, so long as it is not to a toxic level, which a skilled artisan would be able to obtain from the literature (see, for example, van Oosterom et al., 2001). In particular aspects of the invention, the alternative therapy comprises an alternative chemotherapeutic agent, such as SU11248 (Sugen/Pharmacia, South San Francisco, Calif.), 17-AAG, SU11657, AMG706, CHIR258LC, AG-013736, PTK787, Epigallocatechin-3-Gallate (EGCG), or a combination thereof.

V. Diagnostic and Screening Applications

The findings described herein that show the correlation between a specific mutation and imatinib resistance may be used in a number of different assays. For example, the methods described herein can be used in diagnostic or screening assays, wherein individuals are screened for the predisposition to develop resistance to imatinib therapy. The individual may be suspected of having the ability to become resistant, may be substantially refractory to imatinib therapy, or both. In other embodiments of the present invention, the methods are used to confirm the reason for resistance to therapy that has already manifested in the patient.

In view of the fact that a significant number of cases of patients receiving imatinib therapy, such as for GISTs, can be traced to the presence of a particular mutation, a diagnostic application that identifies this mutation is quite useful. Therefore, in one embodiment, the genotype of the KIT gene is determined as described herein, for example. After screening for the mutation, and in the event wherein the mutation is detected, the therapy should be adjusted to avoid deleterious cancer progression upon development of resistance to the therapy.

Also contemplated with the above embodiment of methods of screening for individuals predisposed to developing imatinib resistance are diagnostic kits for the determination of genotype of the KIT gene. The diagnostic kits may comprise, for example, appropriate primers, deoxynucleoside triphosphates; buffers for amplification; labels for the detection of the alleles of interest; control KIT polynucleotides; and instructions for use of said diagnostic kits.

VI. Nucleic Acids

In some embodiments of the present invention, nucleic acids are utilized. For example, KIT polynucleotides may be employed for comparison purposes to facilitate identification of one or more resistance-conferring mutations. Alternatively, a KIT polynucleotide that does not confer resistance to imatinib may be employed in gene transfer to at least one cell comprising a KIT having a resistance-conferring mutation. In other embodiments, KIT primers are utilized in the invention. Thus, the present invention may involve nucleic acids, such as KIT-encoding nucleic acids, nucleic acids identical or complementary to all or part of the sequence of a KIT gene, as well as nucleic acids constructs and primers. In particular aspects of the invention, the KIT nucleic acids comprise an imatinib resistance-conferring mutation. However, given that PDGFR may be involved in some GISTs, it is contemplated that PDGFR polynucleotides, including ones that also confer resistance to therapy, are analogously encompassed in the scope of the invention. For the sake of brevity, the following discussion focuses on KIT as an example, but will analogously also regard PDGFR.

The present invention concerns polynucleotides or nucleic acid molecules relating to the KIT gene and its respective gene product KIT. These polynucleotides or nucleic acid molecules are isolatable and purifiable from mammalian cells. It is contemplated that an isolated and purified KIT nucleic acid molecule, that is a nucleic acid molecule related to the KIT gene product, may take the form of RNA or DNA. As used herein, the term "RNA transcript" refers to an RNA molecule that is the product of transcription from a DNA nucleic acid molecule. Such a transcript may encode for one or more polypeptides.

As used in this application, the term "polynucleotide" refers to a nucleic acid molecule, RNA or DNA, that has been isolated, such as being free of total genomic nucleic acid. Therefore, a "polynucleotide encoding KIT" refers to a nucleic acid segment that contains KIT coding sequences, yet is isolated away from, or purified and free of, total genomic DNA and proteins. When the present application refers to the function or activity of a KIT-encoding polynucleotide or nucleic acid, it is meant that the polynucleotide encodes a molecule that comprises an imatinib resistance-conferring mutation.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 1989; Ausubel, 1996). There may be times when the full or partial genomic sequence is preferred. Alternatively, cDNAs may be advantageous because it represents coding regions of a polypeptide and eliminates introns and other regulatory regions.

It also is contemplated that a given KIT-encoding nucleic acid or KIT gene from a given cell may be represented by natural variants or strains that have slightly different nucleic acid sequences but, nonetheless, encode a KIT polypeptide; a human KIT polypeptide is a preferred embodiment. Consequently, the present invention also encompasses derivatives of KIT with minimal amino acid changes, but that possess the same activity.

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding KIT or a KIT modulator, or a KIT gene or a KIT modulator gene, may comprise a contiguous nucleic acid sequence of the following lengths: at least about 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences may be identical or complementary to, for example, SEQ ID NO:29 (GenBank Accession No. NM_000222), or even the exemplary primers, such as SEQ ID NO:1; SEQ ID NO:2; SEQ ID NO:3; SEQ ID NO:4; SEQ ID NO:5; SEQ ID NO:6, SEQ ID NO:7, SEQ ID NO:8, SEQ ID NO:9, SEQ ID NO:10; SEQ ID NO:11; SEQ ID NO:12; SEQ ID NO:13; SEQ ID NO:14; SEQ ID NO:15; SEQ ID NO:16, SEQ ID NO:17, SEQ ID NO:18, SEQ ID NO:19, SEQ ID NO:26, or SEQ ID NO:27. For the embodiment wherein PDGFR is employed, such sequences may be identical or complementary to, for example, SEQ ID NO:30 (GenBank Accession No. NM_006206), or even the exemplary primers SEQ ID NO:20; SEQ ID NO:21; SEQ ID NO:22; SEQ ID NO:23; SEQ ID NO:24; or SEQ ID NO:25.

In embodiments of the invention, genetic mutations in KIT are relevant. As used herein, a mutation refers to an addition, deletion, or substitution of a single nucleotide at a site in a KIT nucleic acid molecule, for example, that confers resistance to a particular therapy, such as imatinib. Thus, in particular aspects of the invention, an alteration in a sequence results in a change that affects the activity, expression, or stability of a transcript or polypeptide encoded by the sequence such that at least some resistance to therapy, such as the exemplary imatinib, occurs as a result.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated DNA segments and recombinant vectors incorporating DNA sequences that encode a KIT protein, polypeptide or peptide that includes within its amino acid sequence a contiguous amino acid sequence in accordance with, or essentially as set forth in, a KIT sequence comprising a mutation that confers imatinib resistance, such as the Val654Ala mutation.

In particular embodiments, the invention concerns isolated nucleic acid segments and recombinant vectors incorporating DNA sequences that encode KIT polypeptides or peptides that include within its amino acid sequence a contiguous amino acid sequence in accordance with, or essentially corresponding to KIT polypeptides.

The nucleic acid segments used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode KIT or KIT modulators. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs may be prepared that include a contiguous stretch of nucleotides identical to or complementary to all or part of a KIT gene. A nucleic acid construct may comprise at least 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

Certain embodiments of the present invention concern various nucleic acids, including vectors, promoters, therapeutic nucleic acids, and other nucleic acid elements involved in transformation and expression in cells. In certain aspects, a nucleic acid comprises a wild-type or a mutant nucleic acid. In particular aspects, a nucleic acid encodes for or comprises a transcribed nucleic acid.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the KIT gene, other regulatory regions such as enhancers for KIT are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In particular aspects, a nucleic acid encodes a protein, polypeptide, or peptide. In certain embodiments, the present invention concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

A. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic KIT primer that facilitates identification of a imatinib resistance-conferring mutation), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™. (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

B. Purification of Nucleic Acids

A nucleic acid may be purified on polyacrylamide gels, cesium chloride centrifugation gradients, or by any other means known to one of ordinary skill in the art as part of assessment for a mutation that confers resistance to KIT (see for example, Sambrook et al., 1989, incorporated herein by reference). In preferred aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

C. Vectors Encoding KIT

The present invention encompasses the use of vectors to encode for KIT. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment. The promoter may be heterologous or exogenous, for example, a non-KIT promoter with respect to KIT encoding sequence. In some examples, a prokaryotic promoter is employed for use with in vitro transcription of a desired sequence. Prokaryotic promoters for use with many commercially available systems include T7, T3, and Sp6.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements. In certain embodiments of the invention, the use of internal ribosome entry sites (IRES) elements are used to create multigene, or polycistronic, messages.

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. A cell comprising a KIT polynucleotide, either mutated or wild-type, may be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated.

A host cell may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and Solopack.™ Gold Cells (Strategene®, La Jolla). Alternatively, bacterial cells such as E. coli LE392 could be used as host cells for phage viruses.

10. Expression Systems

Numerous expression systems exist that comprise at least a part or all of the compositions discussed above. Prokaryote- and/or eukaryote-based systems can be employed for use with the present invention to produce KIT nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac® 2.0 from Invitrogen® and BacPack™ Baculovirus Expression System from Clontech®.

Other examples of expression systems include Stratagene®'s Complete Control™ Inducible Mammalian Expression System, which involves a synthetic ecdysone-inducible receptor, or its pET Expression System, an E. coli expression system. Another example of an inducible expression system is available from Invitrogen®, which carries the T-Rex™ (tetracycline-regulated expression) System, an inducible mammalian expression system that uses the full-length CMV promoter. The Tet-On™ and Tet-Off™ systems from Clontech® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Nucleic Acid Detection

In some embodiments, the invention concerns identifying mutations in KIT, correlating genotype to phenotype, wherein the phenotype is resistance to imatinib therapy, and then adjusting the therapy of the individual with the mutation if a resistance-conferring mutation is identified. Thus, the present invention involves assays for identifying mutations and other nucleic acid detection methods. Nucleic acids, therefore, have utility as probes or primers for embodiments involving nucleic acid hybridization. They may be used in diagnostic or screening methods of the present invention. Detection of nucleic acids encoding KIT, as well as nucleic acids involved in the expression or stability of KIT polypeptides or transcripts, are encompassed by the invention.

General methods of nucleic acid detection methods are provided below, followed by specific examples employed for the identification of resistance-conferring mutations, or even polymorphisms, including single nucleotide polymorphisms (SNPs).

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in polymerase chain reaction, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to, for example, SEQ ID NOS: 1-19, SEQ ID NOS:26-27, or SEQ ID NOS:33-34 for KIT or, for example, SEQ ID NOS:20-25 for PDGFR, or any other sequence if appropriate, are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as polymerase chain reaction) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

E. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

3. Mutation Detection

Methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP"), polymerase chain reaction, sequencing, hybridization, and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

F. Specific Examples of Mutation-Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases and herein they are referred to as mutations.

The resistance-conferring mutations of the present invention may be of any kind. A variety of single nucleotide mutations have been found that affect a protein-encoding gene in a manner sufficient to actually cause a genetic disease, such as hemophilia, sickle-cell anemia, hereditary hemochromatosis, late-onset Alzheimer disease, and so forth.

In the context of the present invention, mutations that affect the activity and/or levels of the KIT gene products that comprise an imatinib resistance-conferring mutation may be determined by a series of screening methods. One set of screening methods is aimed at identifying mutations that affect the activity and/or level of the KIT gene products in in vitro assays. The other set of screening methods may then be performed to screen an individual for the occurrence of the mutations identified above. To do this, a sample (such as blood or other bodily fluid or cell or tissue sample) is taken from a patient for genotype analysis. The presence or absence of the mutations will determine the ability of the screened individuals to resist imatinib therapy. According to methods provided by the invention, these results will be used to adjust and/or alter the dose of imatinib or to decide on using another agent in order to provide effective cancer treatment. The term "effective cancer treatment" can comprise the eradication of a cancer cell, the cessation or reduction of cancer (such as solid tumor) growth rate, or the amelioration of at least one cancer symptom.

Resistance-conferring mutations can be the result of deletions, point mutations and insertions, for example. In further embodiments, if a particular trait (e.g., ability to confer resistance to imatinib) reflects a mutation at a particular locus, then any polymorphism that is linked to the particular locus can be used to predict the probability that an individual will exhibit that trait.

Several methods have been developed to screen for mutations, and some examples are listed below. Mutations relating to resistance to chemotherapeutic agents can be characterized by the use of any of these methods or suitable modification thereof. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for the proteins encoded by the different alleles of the mutation, or any other biochemical interpretation.

1. DNA Sequencing

The most commonly used method of characterizing a mutation is direct DNA sequencing of the genetic locus that flanks and includes the polymorphism. Such analysis can be accomplished using either the "dideoxy-mediated chain termination method," also known as the "Sanger Method" (Sanger, F., et al., 1975) or the "chemical degradation method," also known as the "Maxam-Gilbert method" (Maxam, A. M., et al., 1977). Sequencing in combination with genomic sequence-specific amplification technologies, such as the polymerase chain reaction may be utilized to facilitate the recovery of the desired genes (Mullis, K. et al., 1986; European Patent Appln. 50,424; European Patent Appln. 84,796, European Patent Application 258,017, European Patent Appln. 237,362; European Patent Appln. 201, 184; U.S. Pat. Nos. 4,683,202; 4,582,788; and 4,683,194), all of the above incorporated herein by reference.

2. Exonuclease Resistance

Other methods that can be employed to determine the identity of a nucleotide present at a mutated site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

3. Microsequencing Methods

Several other primer-guided nucleotide incorporation procedures for assaying mutated sites in DNA have been described (Komher, J. S. et al., 1989; Sokolov, B. P., 1990; Syvanen 1990; Kuppuswamy et al., 1991; Prezant et al., 1992; Ugozzoll, L. et al., 1992; Nyren et al., 1993). These methods rely on the incorporation of labeled deoxynucleotides to discriminate between bases at a mutated site. As the signal is proportional to the number of deoxynucleotides incorporated, mutations that occur in runs of the same nucleotide result in a signal that is proportional to the length of the run (Syvanen et al., 1993).

4. Extension in Solution

French Patent 2,650,840 and PCT Application No. WO91/02087 discuss a solution-based method for determining the identity of the nucleotide of a mutated site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

5. Genetic Bit™ Analysis or Solid-Phase Extension

PCT Appln. No. 92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here, the primer or the target molecule is immobilized to a solid phase.

6. Oligonucleotide Ligation Assay (OLA)

This is another solid phase method that uses different methodology (Landegren et al., 1988). Two oligonucleotides capable of hybridizing to abutting sequences of a single strand of a target DNA are utilized. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR™ are also described (Nickerson et al., 1990). Here, PCR is used to achieve the exponential amplification of target DNA, which is then detected using the OLA.

7. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

8. Methods of Nucleic Acid Transfer

For some methods of the present invention, methods of nucleic acid transfer may be employed. Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

G. Kits

Various kits may be assembled as part of the present invention. A kit may contain components to assay for mutations in KIT to evaluate the ability of a particular patient for the risk of developing resistance to imatinib therapy, and thus allow a clinician to determine whether an alternative treatment for the patient is needed. Such kits may contain reagents that allow for mutations to be evaluated, such as primer sets to evaluate mutations correlated with relevant phenotypic manifestations concerning imatinib resistance. It is contemplated that any of the primers (or pairs of primers) described herein that are complementary to or identical to any of all or part of SEQ ID NO:29, for example, may be part of a kit. For embodiments wherein PDGFR sequence is of concern, SEQ ID NO:25, for example, may be part of a kit. In other embodiments, the kits comprise compositions for detecting a mutation comprising a KIT polypeptide, such as Ab to one or more particular mutations in question. Exemplary reference polypeptides include SEQ ID NO:31 for KIT and SEQ ID NO:32 for PDGRF.

In particular aspects of the invention, there are reagents suitable for use in small pool polymerase chain reaction. For example, one or more of the reagents as described in the Examples for small pooly polymerase chain reaciton may comprised in a kit.

All of the essential materials and reagents required for assaying for KIT mutations by a particular method discussed above may be assembled together in a kit. When the components of the kit are provided in one or more liquid solutions, the liquid solution preferably is an aqueous solution, with a sterile aqueous solution being particularly preferred.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet outlining suggested alternative therapies when particular mutations or SNPs are identified in a patient.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with sample collection and evaluation. Such an instrument may be an inhalant, syringe, pipette, forceps, measured spoon, eye dropper or any such medically approved delivery vehicle, for example.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Methods

Patient and Clinical Trials

Ten patients participated in IRB-approved phase III randomized intergroup trial S00-33, and two patients were treated with imatinib off protocol after the S00-33 intergroup trial was closed. All tumor specimens were obtained with consent on IRB-approved laboratory trial LAB02-433.

Cytogenetic Analyses

Conventional cytogenetic analysis was performed on primary GIST cells from patient A, Clones 1 and 2 after 72-96 hours of culture. The cells were processed by conventional methods using colcemid, potassium chloride, and 3:1 methanol/acetic acid. The chromosomes were then banded by using a trypsin-giemsa (GTG) technique. Twenty metaphases were analyzed.

Genomic DNA and cDNA Sequence Analysis of KIT

DNA was isolated from paraffin-embedded or frozen tissue or peripheral blood mononuclear cells (PBMC) by using a QIAamp DNA mini kit (Qiagen Inc., Valencia, Calif.) according to the manufacturer's instructions. RNA was extracted from frozen tissue. Frozen tissue was ground up with a mortar and pestle, which was chilled with liquid nitrogen. It was then transferred to a 1.5 ml Eppendorf tube containing 1 ml of Tri Reagent (Molecular Research Center, Inc., Cincinnati, Ohio) per 50-100 mg of ground tissue and mixed by vortexing immediately. After 5 minutes of incubation at room temperature, 0.2 ml of chloroform and 1 ml of Tri Reagent was added and mixed by vortexing. After 2-15 min of incubation at room temperature, the samples were centrifuged at 12,000×g for 15 min at 4° C. The aqueous phase was then transferred to a fresh tube, and equal volume of ethanol was added to the aqueous phase, and after mixing, the mixture was loaded onto a Qiagen RNeasy mini column and processed according to the manufacturer's instructions (Qiagen Inc., Valencia, Calif.). The cDNA was prepared by using Two-step Taqman Reverse Transcription Reagent (Applied Biosystems, Foster City, Calif.) according to the manufacturer's instructions except that instead of using random primers, a primer specific for KIT RNA was used (KIT 2961R, 5'-TTCCTGGAGGGGTGACCCAAA-CACT; SEQ ID NO:1)). The cDNA was then subjected to PCR (primers sequence, Table 1). Nucleotide sequencing was analyzed using 3730X1 DNA Analyzer from Applied Biosystems at the M.D. Anderson Cancer Center Nucleic Acid Core Facility. The Genomic DNA sequence of exon 9, 11, 13, 15 and 17 was analyzed (primers 1-5, Table 1) in all GIST specimens, pre-imatinib GISTs and PBMC. RNA was extracted from all surgical specimens. The cDNA sequence from exons 9 to 21 was analyzed, corresponding to the extracellular JM region through the C-terminus (using primers 6-9, Table 1). As KIT cDNA has two alternative splicing sites occurring at codons 510-513 and 715 (Crosier et al., 1993; Zhu et al., 1993), both forward and reverse sequencing were necessary to obtain an accurate sequence when using primers 6 and 8. The hot spot of mutation of PDGFRA are clustered in exon 12 and 18, cDNA of PDGFRA encompassing codon 475-850 will be sequenced using primers 10-12, for example.

TABLE 1

Primer sequence

| No | Type | Primer sequence | | | Codon, Region in KIT |
|---|---|---|---|---|---|
| 1 | Genomic | F: | 5'-CCCAAGTGTTTTATGTATTT | (SEQ ID NO:2) | 449-514, Exon 9 |
|  |  | R: | 5'-ATGGTGTGATGCATGTATTA | (SEQ ID NO:3) |  |
| 2 | Genomic | F: | 5'-TCCAGAGTGCTCTAATGAC | (SEQ ID NO:4) | 550-591, Exon 11 |
|  |  | R: | 5'-AGGTGGAACAAAACAAAGG | (SEQ ID NO:5) |  |
| 3 | Genomic | F: | 5'-TACTGCATGCGCTTGACATC | (SEQ ID NO:6) | 627-664, Exon 13 |
|  |  | R: | 5'-CCAAGCAGTTTATAATCTAGC | (SEQ ID NO:7) |  |
| 4 | Genomic | F: | 5'-TTCTACATGTCCCACTTGATT | (SEQ ID NO:8) | 715-744, Exon 15 |
|  |  | R: | 5'-AGCATGATATACATACTCTCTG | (SEQ ID NO:9) |  |
| 5 | Genomic | F: | 5'-GTGAACATCATTCAAGGCGT | (SEQ ID NO:10) | 788-828, Exon 17 |
|  |  | R: | 5'-CCTTTGCAGGACTGTCAAGCA | (SEQ ID NO:11) |  |
| 6 | cDNA | F: 1265: | 5'-TCCTGACTTACGACAGGCTCGT | (SEQ ID NO:12) | 409-524, Extracellular |
|  |  | R: 1611: | 5'-ACATCATGCCAGCTACGATT | (SEQ ID NO:13) | +TM |

TABLE 1-continued

Primer sequence

| No | Type | Primer sequence | | Codon, Region in KIT |
|---|---|---|---|---|
| 7 | cDNA | F: 1577: 5'-ACACCCTGTTCACTCCTTTGCTGA | (SEQ ID NO:14) | 519-706, TM +Kinase 1 |
| | | R: 2136: 5'-GACTCCTTTGAATGCAGAAGA | (SEQ ID NO:15) | |
| 8 | cDNA | F: 2071: 5'-CGTGATTCATTTATTTGTTC | (SEQ ID NO:16) | 684-830, Kinase Insert |
| | | R: 2510: 5'-CATCCACTTCACAGGTAGTC | (SEQ ID NO:17) | +Kinase 2 |
| 9 | cDNA | F: 2387: 5'-TTCACAGAGACTTGGCAGCCAG | (SEQ ID NO:18) | 789-976, Kinase 2 +C-Terminal |
| | | R: 2961: 5'-TTCCTGGAGGGGTGACCCAAACACT | (SEQ ID NO:19) | |
| PDGFRA | | | | |
| 10 | cDNA | F: 5'-CTGGTGCTGTTGGTGATTGT | (SEQ ID NO:20) | |
| | | R: 5'-TGTTCCTTCAACCACCTTCC | (SEQ ID NO:21) | |
| 11 | cDNA | F: 5'- GCAGCTGCCTTATGACTCAA | (SEQ ID NO:22) | |
| | | R: 5'-TGAGGCTGGACGATCATAGA | (SEQ ID NO:23) | |
| 12 | cDNA | F: 5'-AACCCTGCTGATGAAAGCAC | (SEQ ID NO:24) | |
| | | R: 5'-GGTTGTCAAAGATGCTCTCAGG | (SEQ ID NO:25) | |

Allelic Specific cDNA Sequence

Restriction endonuclease BseRI (New England BioLabs Inc., Beverly, Mass.) was used to preferentially digest the PCR product of the normal allele, but spare the mutated allele of clone 5 of patient C. The digested DNA fragments were separated by agarose gel electrophoresis, eluted from the gel, and sequenced. An alternative method of using mutation-specific primers to preferentially PCR the mutated allele for sequencing was also performed. The counter part normal allele was also sequenced for comparison.

Immunohistochemistry (IHC)

Primary polyclonal antibodies against KIT (Santa Cruz Biotechnology, Santa Cruz, Calif.) and phosphorylated tyrosine peptide specific antibodies against pY703, pY721, pY730, and pY823 of KIT (Biosource International, Camarillo, Calif.) were used for IHC. One phosphotyrosine peptide specific antibody recognizes both Tyr568 and Try570. Frozen sections were processed by standard procedures. This was followed by a standard avidin-biotin peroxidase complex assay (Vector Laboratory, Burlingame, Calif.). Slides were developed with DAB (Zymed Laboratories, Santa Cruz, Calif.) and counterstained with 10% hematoxylin.

Example 2

Patients and Clinical Course

The clinical course of GIST patients varies, most patients continue to enjoy remission, but a small percent of GIST patients who had initial near complete response, subsequently showed mixed response with the emergence of new liver lesion(s) or rapidly progressing imatinib-resistant implant(s) while the rest of implants and or liver metastases remained responsive to imatinib. At present time, among approximately 130 patients, the present inventors have identified 5 patients who unequivocally developed imatinib resistance under close surveillances by radiographic criteria and were amenable for biopsy or surgical resection of the resistant implants, and all 5 patients (designated as patients A-E, Table 2) were included in this study.

TABLE 2

KIT sequence of pre-imatinib, post-imatinib residual GISTs and clones 1-11

| Patients (A-L) and characteristics of GIST specimens | KIT sequence | | |
|---|---|---|---|
| | Exon 11 | Exon 9 | Exon 13 |
| A: Pre-imatinib | 1690T→G | Normal | Normal |
| A: Clone 1: Rapid progression | 1690T→G | Normal | 1982T→C (Val654Ala) |
| A: Clone 2: Rapid progression | 1690T→G | Normal | 1982T→C (Val654Ala) |
| A: Clone 3: Stable/Quiescent | 1690T→G | Normal | Normal |
| B: Pre-Imatinib | 1691-1696del6 | Normal | Normal |
| B: Clone 4: Rapid progression | 1691-1696del6 | Normal | 1982T→C (Val654Ala) |
| C: Pre-imatinib | 1694-1708del15 | Normal | Normal |
| C: Clone 5: Rapid progression | 1694-1708del15 | Normal | 1982T→C (Val654Ala) |
| C: Clone 6: Stable/Quiescent | 1694-1708del15 | Normal | Normal |
| C: Clone 7: Stable/Quiescent | 1694-1708del15 | Normal | Normal |
| D: Pre-imatinib | 1690-1695del6 | Normal | Normal |
| D: Clone 8: Rapid progression | 1690-1695del6 | Normal | 1982T→C (Val654Ala) |
| D: Clone 9: Stable/Quiescent | 1690-1695del6 | Normal | Normal |
| E: Clone 10: Pre-imatinib | Normal | 1525-1530ins6 | Normal |

TABLE 2-continued

KIT sequence of pre-imatinib, post-imatinib
residual GISTs and clones 1-11

| Patients (A-L) and characteristics of GIST specimens | KIT sequence | | |
|---|---|---|---|
| | Exon 11 | Exon 9 | Exon 13 |
| E: Clone 11: Rapid progression | Normal | 1525-1530ins6 | 1982T→C (Val654Ala) |
| F, G, H, I: Residual: Stable/Quiescent | Normal | 1525-1530ins6 | Normal |
| J: Residual: Stable/Quiescent | 1697T→G | Normal | Normal |
| K: Residual: Stable/Quiescent | 1697-1708del12 | Normal | Normal |
| L: Residual: Stable/Quiescent | 1700T→G | Normal | Normal | del: deletion;
Ins: insertion;
Exon 11: 1690T→G ⇒ Try557Gly, 1691-1696del ⇒ TryLys$^{557-558}$ deletion plus Val559Phe, 1694-1708del ⇒ LysValVal GluGlu$^{558-562}$ deletion, 1690-1695del ⇒ TryLys$^{557-558}$ deletion, 1697T→G ⇒ Val559Gly, 1697-1708del ⇒ ValVal GluGlu$^{559-562}$ deletion, 1700T→G ⇒ Val560Gly;
Exon 9: 1525-1530ins ⇒ AlaTyr$^{502-503}$ tandem repeat.

Some GIST patients had initial near complete remission followed by a plateau showing persistent stable residual tumor. The present inventors have identified 7 such patients who were amenable for surgical resection of the residual quiescent GISTs and all 7 patients (designated as patients F-L, Table 2) were included in this study. Except for patients C and F, 10 patients participated in S00-33 intergroup trial, and all were randomized to the imatinib 400 mg/day arm. All 12 patients were treated with 400 mg imatinib a day.

FIG. 1 shows CT, positron emission tomography (PET) and PET CT scan images of patient A (a-1-10), patient B (b-1-4), patient C (c-1-2) and patient D (d-1-2). In (a-1) and (a-2), there are pre-imatinib CT images of patient A showing multiple peritoneal tumor implants. In (a-3) and (a-4), there are CT images obtained at 8 weeks post imatinib treatment demonstrating rapid resolution of most of peritoneal tumor implants. In (a-5) and (a-6), there are CT images 28 months post imatinib treatment demonstrating two new imatinib-resistant implants in the small bowel mesentery (arrows, a-5, clone 1; a-6, clone 2). In (a-7), there is pre-imatinib PET showing multiple hypermetabolic tumor implants. In (a-8), there are PET images 8 weeks post-imatinib treatment demonstrating near total resolution of all hypermetabolic tumors. In (a-9) and (a-10), there are PET CTs 28 months post imatinib treatment that revealed two new discrete hypermetabolic tumor implants (two yellow spots, each is pointed to by an arrow), corresponding to the resistant clone 1 (arrow) and clone 2 (arrow). In (b-1), there are pre-imatinib CT images of patient B showing multiple liver metastases and matted peritoneal implants. In (b-2), there is a CT of abdomen obtained 4 months after imatinib treatment showing near total resolution of all implants and hypoattanuating liver lesions indicating necrosis or good response. In (b-3) and (b-4), there is CT of abdomen 6 and 9 months post imatinib treatment respectively. A suspicious tiny implant (arrow, resistant clone 4) was noted between spleen and stomach. Rapid progression of clone 4 (arrow, b-4) was noted within three months. In (c-1) and (c-2), there are CT scans of patient C pre-imatinib and 8 weeks post imatinib. One of the implants in left upper quadrant bears a surgical clip (FIG. 1c-1, a dense white tiny rod at 4 o'clock) that can be identified and traced to an implant that is much reduced in size 8 weeks post imatinib (FIG. 1c-2, a tiny dense white dot at 3 o'clock). In (c-3) and (c-4), nineteen months later a small implant was noted (FIG. 1c-3, short arrow, clone 5), which was not present in previous CT scans performed at 8 weeks or 16 months post-imatinib treatment and represented an imatinib-resistant implant with rapid progression (FIG. 1c-4, arrow, clone 5). Two quiescent nodules from omentum were also removed and are designated as clones 6 & 7 (Table 2). In (d-1) and (d-2), CT scans of patient D show initial excellent response. In (d-3) and (d-4), there is rapid progression of a tiny tumor implant (arrow, resistant clone 8) in the omentum.

Figure 2:
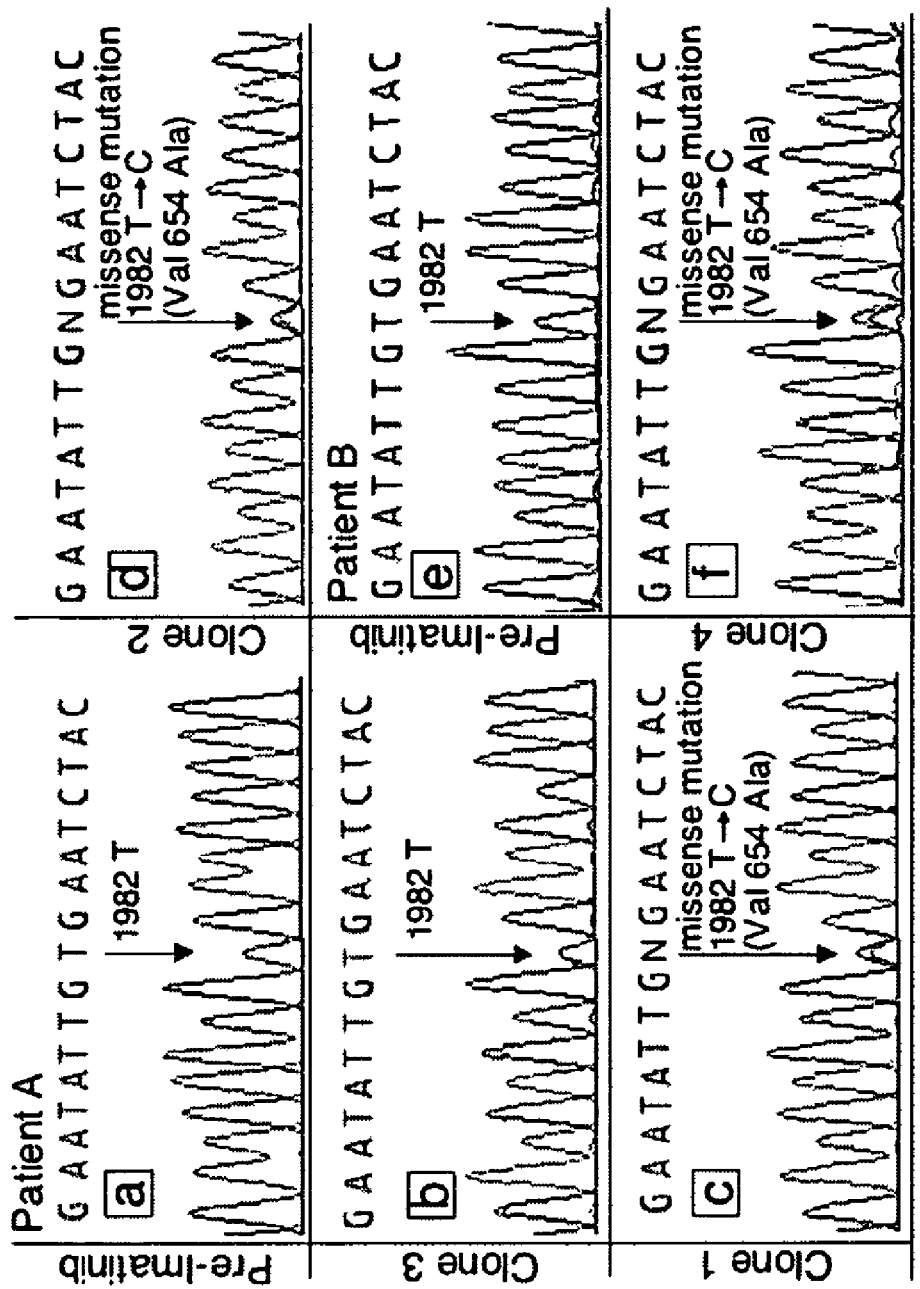
FIGS. 2A-2F provide the chromatograms of KIT mutation of patient A (2A-2D) and patient B (2E-2F) demonstrating that a novel missense mutation in KIT exon 13 correlates with imatinib-resistant rapid progression of GISTs.

The pre-imatinib CT scan of patient A revealed multiple single and matted peritoneal implants in the patient's abdomen (FIG. 1a-1) and pelvis (FIG. 1a-2). Patient A had a swift excellent response with near total resolution of GISTs and marked reduction of abdominal girth within 8 weeks of imatinib treatment (FIG. 1a-3, a-4). Positron emission tomography (PET) scans showed initial multiple hypermetabolic tumor implants followed by near total resolution of all hypermetabolic activities 8 weeks after imatinib therapy (FIG. 1a-7, a-8). Patient A continued to respond to imatinib until 25 months later when a small new implant appeared in the small bowel mesentery and progressed rapidly within 3 months (FIG. 1a-5, clone 1). Subsequently, a second small implant (clone 2) became visible on CT scan (FIG. 1a-6, clone 2). PET CT scan revealed two discrete small areas of intense hypermetabolic tumor (yellow spots indicated by arrows in FIG. 1a-9, a-10) that corresponded to clones 1 and 2 respectively. The doubling time of clone 1 was calculated to be 35 days. Intra-operatively, clones 1 and 2 were found to be purple-brownish vascular viable tumor implants and were surgically removed. Surprisingly, there were more than two hundred small white, soft, quiescent appearing nodules found throughout patient A's abdomen and pelvis, not readily visible on CT scans. Complete debulking was not possible, a representative specimen was removed for diagnosis and is designated as clone 3 (Table 2). These quiescent nodules showed extensive treatment effect with very small areas of viable GIST cells seen on histological examination. Within 8 weeks of imatinib treatment, most of GISTs resolved, but small pockets of cells escaped apoptosis and remained quiescent and survived for more than 2 years in patient A.

Patient B presented with multiple liver metastases and single and matted peritoneal implants, some coalescing into large masses (FIG. 1b-1). CT scans 8 weeks (data not shown) and 4 months after imatinib treatment (FIG. 1b-2) were very similar and showed near total resolution of all implants and the appearance of hypoattanuating liver lesions indicating necrosis and a good response to treatment. A new implant (FIG. 1b-3, arrow, clone 4) appeared 6 months after imatinib treatment and was visible as a tiny implant between the spleen and the contrast-filled stomach. Within 3 months, clone 4 progressed into a huge implant (FIG. 1b-4, arrow) with an estimated doubling time of 10 days. All other implants and liver lesions remained sensitive to imatinib. Complete resection of clone 4 was not possible and biopsy was performed.

Patient C presented with multiple implants in left upper quardrant, one of which bear a surgical clip (FIG. 1c-1, a dense white tiny rod at 4 o'clock) that can be identified and traced to an implant much reduced in size 8 weeks post imatinib (FIG. 1c-2, a tiny dense white dot at 3 o'clock). Nineteen months later when a small implant was noted (FIG. 1c-3, short arrow, clone 5), which was not present in previous CT scans performed at 8 weeks or 4 months post-imatinib treatment and represented a imatinib-resistant implant with rapid progression (FIG. 1c-4, arrow, clone 5). Two quiescent nodules from omentum were also removed and are designated as clones 6 and 7 (Table 2). Patient D had initial excellent response as shown in FIG. 1-d-1 and d-2 and developed a small new implant (FIG. 1d-3, arrow, clone 8) 19 months after imatinib treatment and this implant progressed rapidly within 4 months (FIG. 1d-4, arrow, clone 8). Patient E developed an imatinib-resistant rapidly growing implants 31 months after imatinib treatment (CT scans not shown). Patients C, D and E underwent surgery immediately at the onset of imatinib resistance and clones 5-11 (Table 2) were surgically removed from these 3 patients respectively.

Patients F-L underwent surgical resection of stable/quiescent residual GISTs at the time when the response to imatinib reached plateau.

Example 3

Kit Mutation Prior to Imatinib Treatment

Direct sequencing of KIT genomic DNA (exons 9, 11, 13, 15, 17) was performed on all GISTs, including paraffin-embedded specimens. Direct sequencing of cDNA was performed on clones 1-11 and all surgical and biopsy specimens of GISTs. The results of KIT mutations, deletions (del) and insertion (ins) of all 12 patients are summarized in Table 2. The corresponding amino acids changes in KIT are listed in the footnote of Table 2. The initiating events that cause constitutively active KIT of patients A-D and J-L involved different mutation sites in exon 11 (ranging from nucleotides 1690 through 1708) resulting in amino acid changes (ranging from Try557 to Glu562) in cytoplasmic juxtamembrane region. Patients E-I showed 6 b.p insertion in exon 9 and resulting in tandem repeat of AlaTyr502-503 in extracellular juxtamembrane region.

Example 4

Development of a New Missense Mutation in Kit Kinase Domain 1 is Correlated with the Emergence of Imatinib Resistance in GISTs After Initial Excellent Response FIGS. 2A-2F provide the chromatograms of KIT mutation of patient A (2A-2D) and patient B (2E-2F) demonstrating that a novel missense mutation in KIT exon 13 correlates with imatinib-resistant rapid progression of GISTs. FIG. 2A provides genomic DNA sequence from pre-imatinib GIST of patient A, showing the wild type 1982T. FIG. 2B shows genomic DNA sequence from the residual quiescent clone 3, showing wild type 1982T. FIG. 2C shows genomic DNA sequence from the imatinib-resistant rapidly growing clone 1, showing a new missense mutation, 1982T→C, resulting in Val654Ala. FIG. 2D shows genomic DNA sequence from the imatinib-resistant rapidly growing clone 2 show the same new 1982T→C mutation. FIG. 2E shows genomic DNA sequence from pre-imatinib GIST of patient B showing wild type 1982T. FIG. 2F provides genomic DNA sequence from imatinib-resistant rapidly growing clone 4 show the same new 1982T→C mutation.

Figure 3:
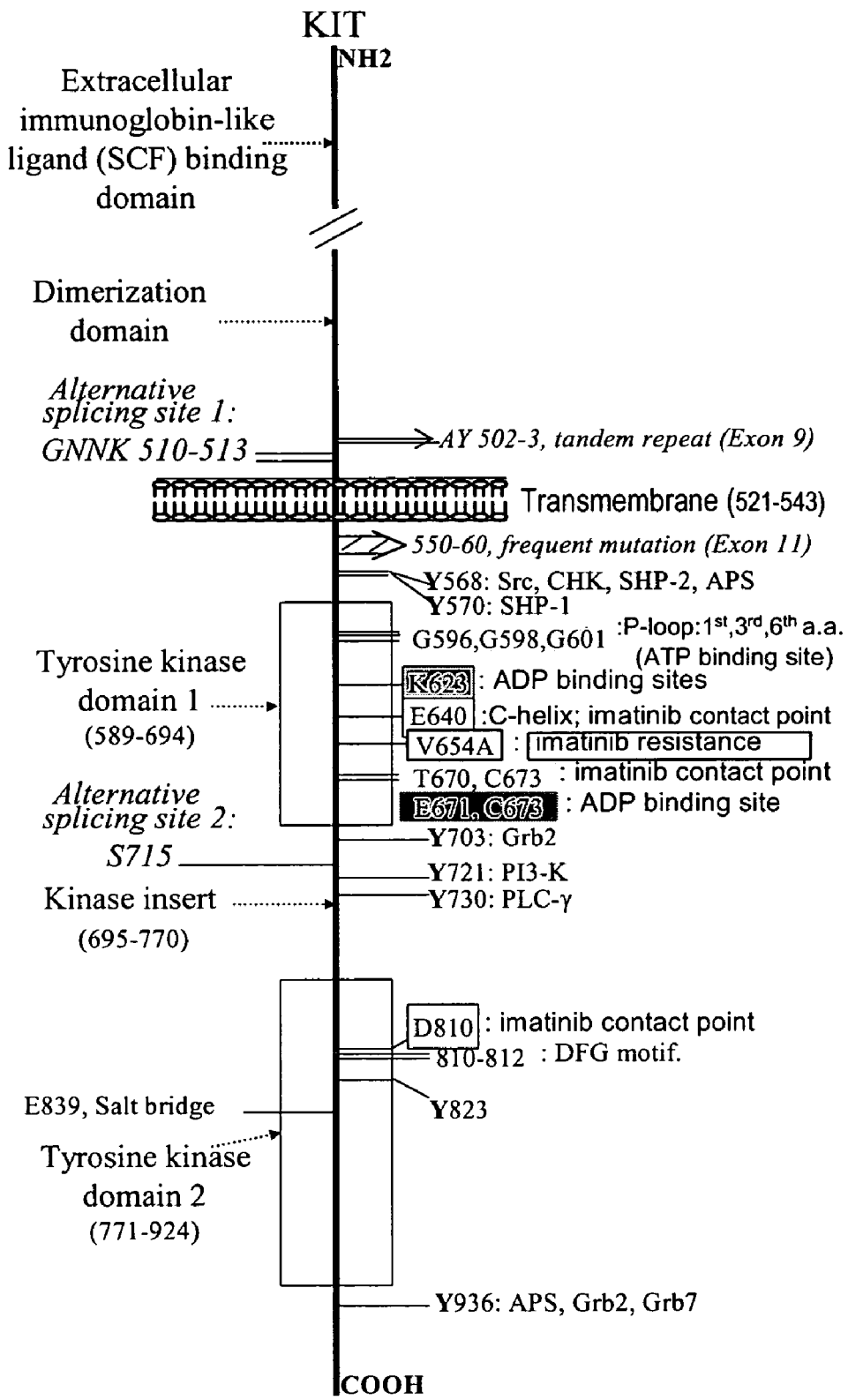
FIG. 3 illustrates some structural and functional regions of KIT. Imatinib contact points are noted, as are the P-loop sites, the ADP binding sites, and the Val654Ala mutation.

Most strikingly, all 6 imatinib-resistant rapidly growing clones 1, 2, 4, 5, 8, (FIG. 1, arrows) and clone 11 (CT scan not shown) from 5 patients (A-E) showed an identical novel exon 13 missense mutation, 1982 T→C (FIG. 2C, 2D, 2F; Table 2), resulting in a substitution of Val by Ala at codon 654 (Val654Ala) in tyrosine kinase domain 1 of KIT (FIG. 3). This new mutation has never been reported in literature before and is not found in any pre-imatinib GISTs (FIG. 2A, Table 2) of any one of the 12 patients or any one of the residual quiescent clones 3 (FIG. 2B), 6, 7, 9 or any residual stable quiescent post-imatinib-GISTs from patients F-L or PBMC of patients A-E. Both genomic and cDNA sequence in both forward and reverse directions were performed to confirm this new mutation. Since this novel exon 13 mutation identified in imatinib-resistant rapidly growing clones 1, 2, 4, 5, 8, 11 from patients A-E are identical, the representative chromatograms of patients A and B are provided (FIG. 2). These data indicate that this novel 1982 T→C missense mutation is nonrandom and is strongly correlated with imatinib resistance and rapid progression of GIST.

Example 5

Figure 4A:
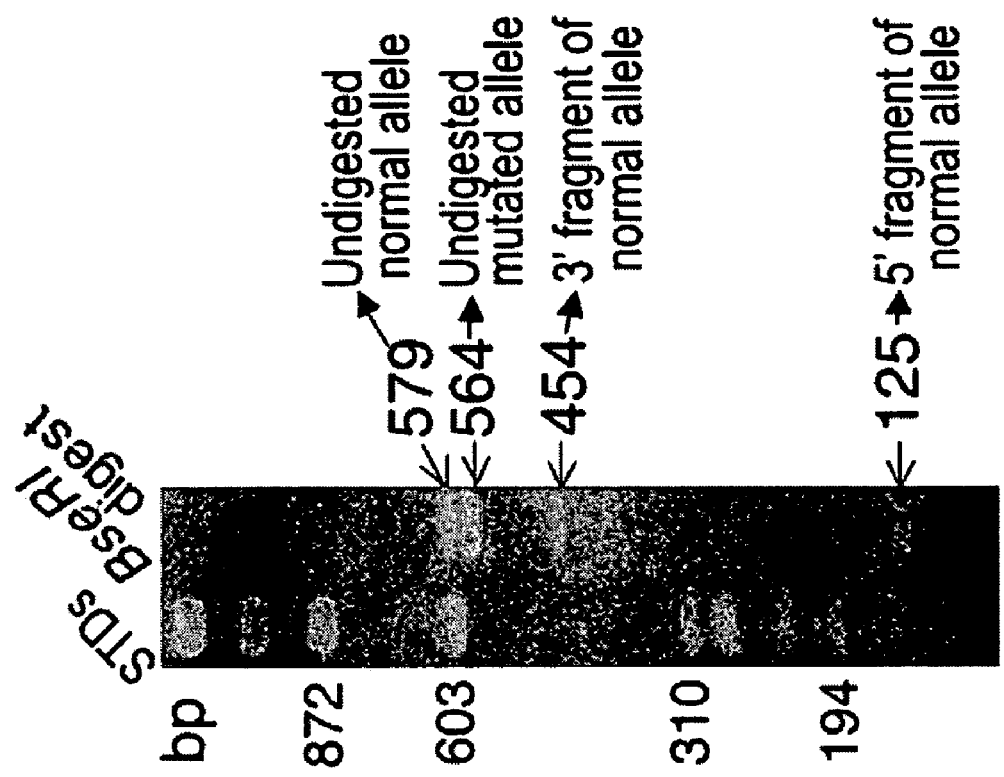
FIGS. 4A-4B show allelic-specific sequencing data of clone 5 from exemplary patient C. Using primer #7 (Table 1) and polymerase chain reaction, cDNAs (encompassing exons 10-14) were generated, digested with BseRI, separated on 2% agarose gel electrophoresis, eluted from a gel and sequenced.
Figure 4B:
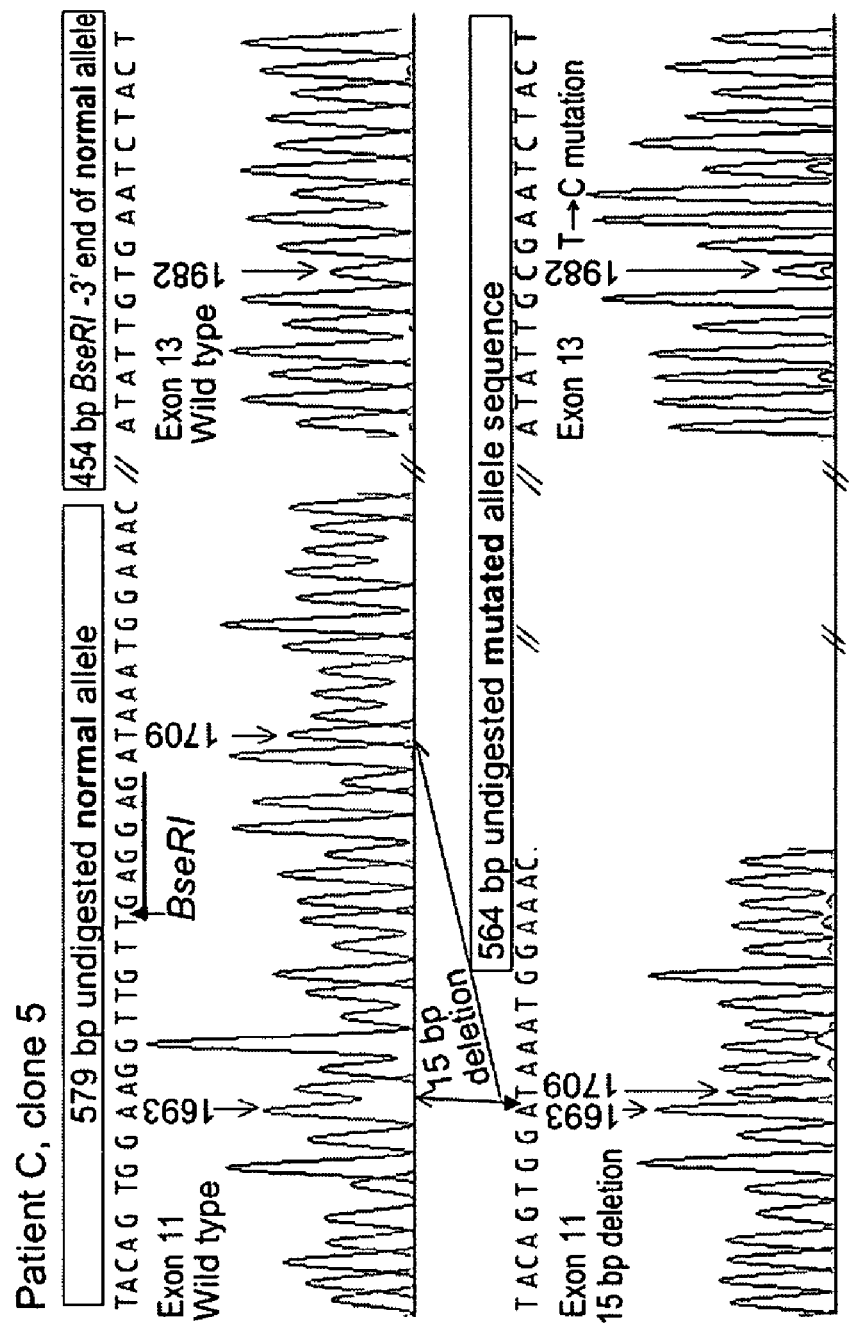

Allelic-Specific Sequence Analyses Demonstrate the Occurrence of the Novel 1982 T→C Missense Mutation in the Original Mutated Allele The 1982T→C mutation is heterozygous as shown in FIG. 2. Allelic-specific sequence analyses were performed to determine whether this additional event of 1982T→C mutation in KIT occurs in the wild type or the original mutated allele that bears the dominant activation exon 11 or exon 9 mutation. Clone 5 from patient C shows a 15 bp deletion in exon 11 (Table 2). This deleted 15 bp (1694-1708, AGGT-TGTTGAGGAGA; SEQ ID NO:28), interestingly, contains the unique restriction endonuclease BseRI recognition site, GAGGAG. Primer #7 was used (Table 1) in PCR to generate cDNA that encompass exon 10-14. A 579 bp (wild type allele) and a 564 bp (1694-1708del15) cDNA were generated. Restriction endonuclease mapping shows that BseRI will cut the wild type 579 bp DNA only once and spare the 564 bp cDNA which is devoid of the BseRI recognition site. An example of BseRI partial digestion followed by agarose gel electrophoresis (2%) is shown in FIG. 4A. Four bands including a 579 bp (top band) undigested normal allele, a 564 bp undigested cDNA from mutated allele, a 125 bp 5' end of digested fragment and a 454 bp 3' end of digested fragment (containing exon 13) from normal allele can be visualized. Upon complete digestion by BseRI, the 579 bp DNA became completely digested and only 3 bands can be visualized. Direct sequencing of DNA eluted from these 4 bands were performed and the sequences are shown in FIG. 4B. The upper left panel show that the 579 bp DNA, which represents the undigested normal allele, exhibiting wild type exon 11 sequence with the intact BseRI recognition site, GAGGAG. The lower panel shows that the undigested 564 bp DNA, which was derived from the original mutated allele, contain both the 15 bp deletion and 1982T→C mutation. The 454 bp 3' end fragment derived from normal allele DNA show wild type 1982T (top right panel). For patients A, B, D and E, mutation-specific primers were used to selectively PCR the mutated allele for sequencing. The normal allele counterparts were also examined for comparison. The second exon 13 (1982T→C) mutation was found in the original mutated allele in all 6 imatinib-resistant clones in all 5 GIST patients.

Example 6

Constitutive Activation of Kit in Imatinib-Resistant GIST

Figure 5:
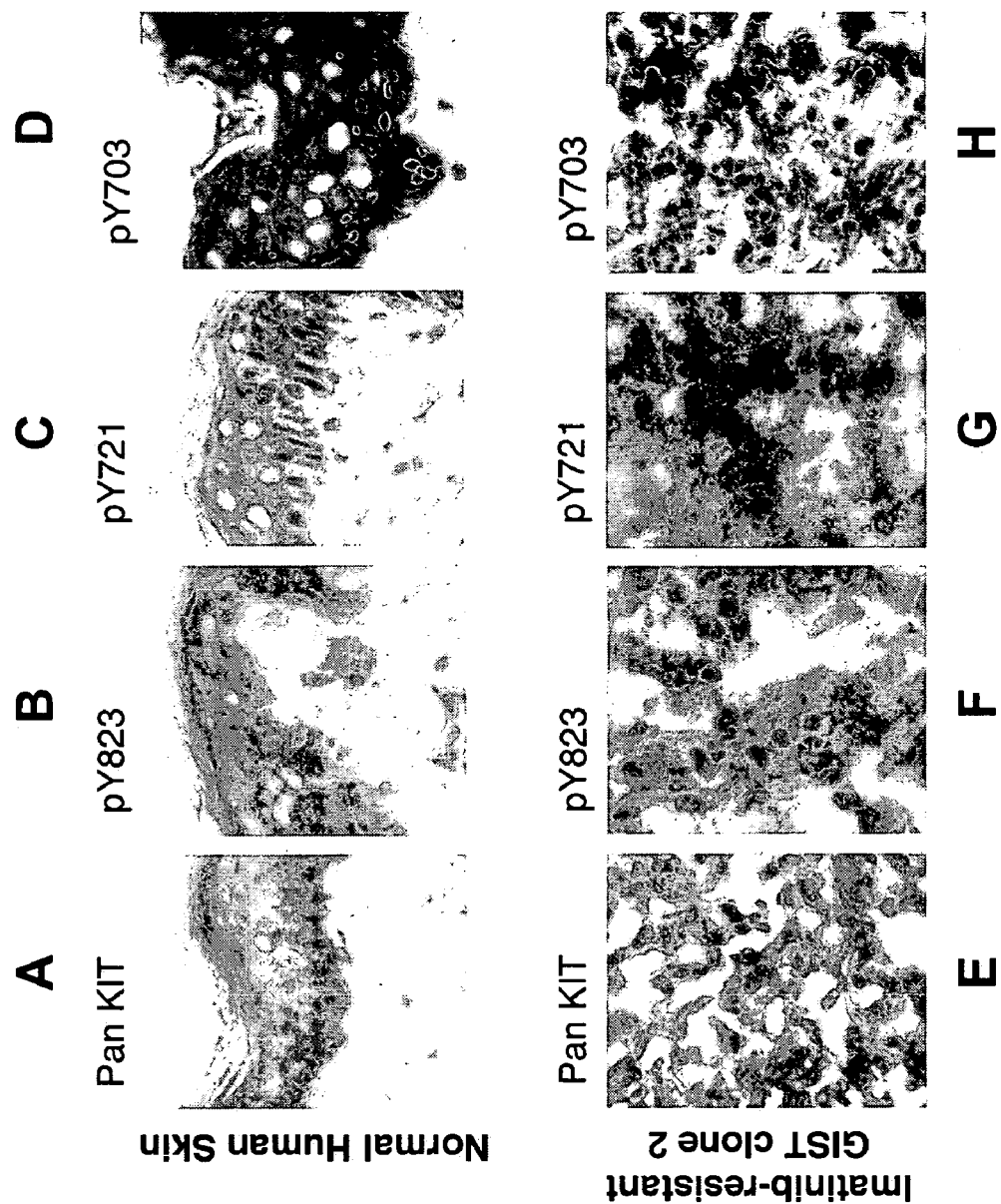
FIGS. 5A-5H show constitutive activation of KIT in imatinib-resistant GIST clone 2 of exemplary patient A. Top panels provide frozen IHC of human normal skin as control. Epidermal melanocytes express strong positive staining of pan-KIT and pY703, and weak staining of pY823 and pY721, while keratinocytes (internal negative controls) and other dermal cells fail to express KIT or any of the three phosphorylated tyrosine residues, pY823, pY721 or pY703. Lower panels provide frozen IHC of imatinib-resistant clone 2 that show strong expression of pan-KIT and pY703 and moderate staining with pY823 and pY721, indicative of reactivation of KIT in imatinib-resistant GIST. Empty spaces are due to freezing artifact. All micrographs show the same magnification.

Imatinib forms stable complexes with KIT, and thus prevents binding of ATP with KIT kinase domain, resulting in blockage of autophosphorylation of tyrosine residues of Y568/570, Y703, Y721, Y730, Y823 and Y936, leading to inhibition of KIT constitutive activity and resulting in apoptosis and or necrosis of GISTs. The reversal of imatinib effects and restoration of constitutive KIT activity in imatinib-resistant GIST clone 2 of patient A is shown in FIG. 5. The rapidly proliferating clone 2 was composed of fascicles of spindle and epithelioid cells and more than 15 mitotic figures/HPF (data not shown). The present inventors used normal human skin as positive and negative control for the frozen IHC. FIG. 5 top panels show the positive expression of pan-KIT, pY823, pY721 and pY703 of KIT in epidermal melanocytes, while keratinocytes (internal negative controls) and other dermal cells show negative staining. Lower panels show the frozen IHC of imatinib-resistant GIST clone 2 demonstrating the positive expression of KIT, pY823, pY721 and pY703 of KIT. The second mutation of Val654Ala in KIT in specific embodiments changed the conformation of KIT kinase domain and significantly reduced the binding affinity of imatinib with KIT, reactivated autophosphorylation of the various tyrosine residues of KIT, and manifested the imatinib-resistant GIST phenotype.

IHC Analysis on Frozen Sections

Primary polyclonal antibody against KIT (pan KIT antibody; Santa Cruz Biotechnology, Santa Cruz, Calif.) was used for IHC analysis on normal human skin and GISTs to assess the expression of KIT. Polyclonal antibody against KIT peptide-specific phosphorylated Tyr823 (pY823), pY721 and pY703 (Biosource International, Camarillo, Calif.) were used for IHC on frozen sections of normal human skin and imatinib-resistant GIST clone 2 to assess the phosphorylation status of Y823, Y721 and Y703 and, thus, KIT activation. The human normal skin and GISTs were oriented and embedded in OCT media and cryosectioned into 6 μm sections. Slides were fixed in cold acetone for 1 minute and rehydrated in PBS. They were blocked in 3% $H_2O_2$ in PBS, followed by 3% normal goat serum. The slides were then incubated overnight at 4° C. with pan KIT and verious pY antibody (1:100). Standard procedures using biotinylated secondary antibody followed by streptavidin-horseradish peroxidase were employed, and development utilized a DAB kit (Zymed Laboratories, Santa Cruz, Calif.), and counterstaining with 10% Hematoxylin.

Example 7

Crystal Structures of Wild-Type and Mutant Kit

In a case report of imatinib resistant metastatic GIST, Tamborini et al. (2004) reported a second new mutation, 2030C→T in exon 14 of KIT, resulting in replacement of Thr at codon 670 by Ile (T670I), in addition to the first exon 11 activation mutation. In another single case report of imatinib-resistant GIST, Wakai et al. (2004) found a different new second mutation in exon 17 resulting in replacement of Tyr at codon 823 by Asp (Y823D), in addition to the initial exon 11 activation mutation in KIT.

The present inventors studied 12 GIST patients with initial near complete response to imatinib. Seven harbored mutations in KIT exon 11 and 5 harbored mutations in exon 9. Within 31 months, 6 imatinib-resistant rapidly progressive peritoneal implants (metastatic foci) developed in 5 patients. Quiescent residual GISTs persisted in 7 patients. All 6 rapidly progressive imatinib-resistant implants from 5 patients showed an identical novel KIT missense mutation, 1982T→C, resulting in the replacement of Val at codon 654 with Ala (V654A) in the KIT tyrosine kinase domain 1. The frequency of the three kinase domain mutations, V654A, T670I and Y823D, in imatinib resistant GISTs remains unknown, although in specific embodiments, the most common form is the V654A mutation.

Mol et al. reported the crystal structural of KIT (2004), and the present inventors obtained the structure coordinates (IT46) from the Protein Data Bank and used Swiss-Pdb-Viewer (Guex and Peitsch, 1997) to visualize the three-dimensional (3-D) structure of wild type and mutated KIT. The crystal structure of KIT in complex with imatinib is shown in FIG. 6A. The Y823 forms critical hydrogen bonds with R796 and D792, and T670 forms a critical hydrogen bond with imatinib. The 3-D structures of the mutated and imatinib-resistant KIT (V654A, T670I and Y823D) are shown in FIGS. 6B, 6C and 6D, respectively. A comparison of the wild type KIT (FIG. 6A) with the V654A mutated KIT (FIG. 6B) shows that the switch from Val to Ala at codon 654 eliminates hydrophobic interactions of the methyl groups with the aromatic rings in imatinib, thereby reducing the binding of imatinib with KIT. The comparison of wild type KIT (FIG. 4A) with the T670I mutated KIT (FIG. 6C) shows the elimination of a critical hydrogen bond with imatinib. This hydrogen bond can be seen in FIG. 6A, and the elimination of the hydrogen bond in FIG. 6C, reduces the binding of imatinib with KIT. Finally, a comparison of wild type KIT (FIG. 6A) with the Y823D mutated KIT (FIG. 6D) shows the loss of hydrogen bonds with Arg796 and Asp792, resulting in structural change that impedes the access or fit of imatinib with KIT, in specific embodiments.

Figure 6:
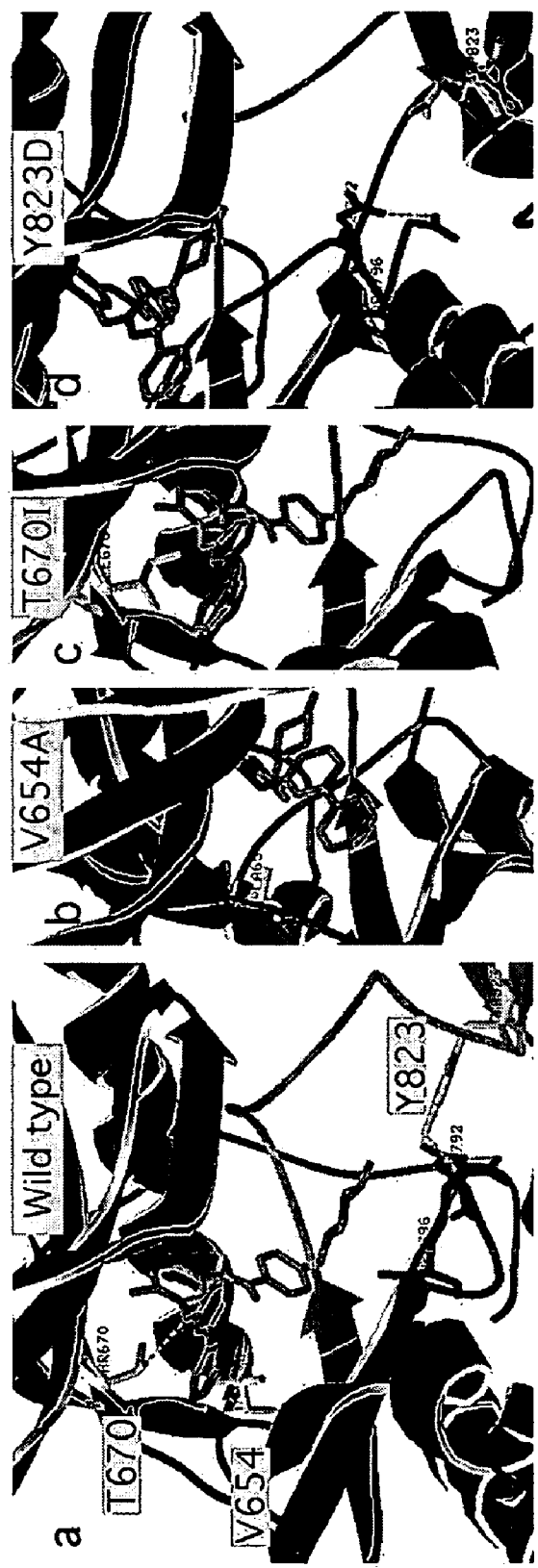
FIGS. 6A-6D show crystal structures associated with KIT.

The data presented in FIG. 6 demonstrated that the Val654Ala mutation in kinase domain1 of KIT resulted in 3-D configurational changes, which in turn resulted in decreased affinity with imatinib. With significant reduction of binding of imatinib with KIT, these GIST cells restored their constitutive kinase activity of KIT as demonstrated in reactivation of autophosphorylation of the various tyrosine residues as shown in FIG. 5. These data proved that the mechanism of imatinib resistance in these GISTs harboring the second Val654Ala mutation is KIT-dependent, and convincingly excluded the possibility of activation of down stream signals as the cause of imatinib resistance, in these embodiments.

Example 8

Pre-Existing Mutation for Imatinib Resistance

In some embodiments, the one or more mutations that confer resistance to imatinib are present prior to treatment with imatinib, and in further embodiments the mutation(s) is present prior to the onset of GIST. For example, the mutation(s) that confers drug resistance may be pre-existing at extremely low frequency prior to treatment. Under the selection pressure of drug treatment, the mutated clone outgrows and results in drug resistance and rapid progression.

In particular aspects of the invention, the frequency of pre-existing mutation(s) that has the potential to confer imatinib-resistance is determined. The novel KIT missense mutation, 1982T→C, is undetectable in pre-imatinib GISTs by PCR using normal primers, suggesting it is present at a very low frequency. PCR using mutation-specific primer(s) that comprise the mutation at the 3' end of the forward primer, for example, has been tested and can detect this 1982T→C mutation in pre-imatinib GIST using DNA extracted from either paraffin-embedded or frozen GIST, for example. Small pool PCR will be used to quantitatively estimate the frequency of KIT 1982T→C mutation in pre-imatinib GISTs. There are more than 120 imatinib responsive GIST patients that are currently available to the present inventors, and the duration of imatinib-resistance ranges from 6 months to more than 3 years at present time. Correlation of the pre-imatinib mutation frequency and the duration of response to imatinib will be analyzed. In the embodiments where positive correlation is established, the mutation can serve as a "tumor marker", a predictor for prognosis and response, and it will have significant impact in treatment decision as more KIT/PDGFRA targeted drugs become available.

A means to identify the mutation, such as to assess if there is a pre-existing nature to the mutation, is provided. In particular aspects, the mutation is identified directly by polymerase chain reaction, for example. In some embodiments, by using normal primers, the novel KIT mutation (1982T→C) is not detected in PBMC or pre-imatinib GISTs by standard PCR means, indicating there is a very low frequency. To circumvent this issue, the present inventors designed a mutation-specific primer, F: 5'-CCTTGGTAAT-CACATGAATATTGC-3' (SEQ ID NO:26), and R: 5'-CCAAGCAGTTTATAATCTAGC-3' (SEQ ID NO:27), comprising the mutated 1982 C at the 3' end of the Forward primer. By using the exemplary mutation-specific-primer, the present inventors are able to detect the existence of 1982T→C in the pre-imatinib GISTs in those patients who became imatinib-resistant. Among the 120 GIST patients, approximately 10% has intrinsic resistance and never responded to imatinib. The imatinib clinical trial registered 106 GIST patients from December 2000 to September 2001, and most patients continue to enjoy near complete response. Approximately 5-8% patients who had initial excellent response later developed imatinib-resistance. There are at least 5 GIST patients (Table 1) who developed one or two rapidly growing implants within a period of 6-35 months after imatinib treatment. In an object of the invention, the duration of response to imatinib is correlated with the frequency of 1982T→C mutation in the pre-imatinib GIST.

Example 9

In Vitro Model of Imatinib Resistance

In some aspects of the invention, an in vitro model of imatinib resistance is produced. This may be generated by any means suitable in the art, although in a specific embodiment the cDNA of KIT harboring the Val654Ala mutation that confers imatinib resistance will be amplified by PCR and subcloned in an expression vector. The mutated KIT will be transfected into imatinib-sensitive GIST cell lines for signal transduction studies and in vitro screening of new pipeline drugs and drugs in early phase trials, such as 17-AAG, SU11248, SU11657, AMG706, CHIR258LC, AG-013736, PTK787, Epigallocatechin-3-Gallate (EGCG), and so forth. Pre-clinical in vitro studies, such as one utilizing this model, are utilized for selecting appropriate drug(s). Any new drug that can overcome at least some imatinib resistance is desired.

In exemplary embodiments, an in vitro model of imatinib resistance is generated as follows:

Construction of expression vector: The present inventors have sequenced cDNA of 37 GISTs, and 7 have normal KIT, 8 show exon 9 mutation (codon 502-3 tandem repeat) and 20 harbor various exon 11 mutations. The whole coding region of human wild type KIT can be amplified from the cDNA obtained from the 7 GISTs without a KIT mutation. KIT with various mutations in exon 11 or exon 9 can be obtained from any one of the 37 GISTs exhibiting the specific mutations.

Allelic-specific sequencing data has shown that the 1982T→C mutation, occurred in the original allele bearing the dominant activation exon 11 or exon 9 mutation. The Coding region of human KIT cDNA containing this 1982T→C mutation can be amplified by PCR from cDNA of any one of the imatinib-resistant GIST clones 1, 2, 4, 5 or 8 (Table 1). These various mutated KIT and wild type cDNA can be subcloned into the expression vector pcDNA3.1 containing cytomegalovirus promoter and pCI-neo (Eder et al., 1998; Zou et al., 2002; Li et al., 2003).

Transfection of wild type and mutated kit into imatinib-sensitive cell lines: ST882 GIST cell line has the activation kit exon 13 homozygous 1945A→G mutation, which is 12 amino acids N-terminal to the novel 1982T→C mutation reported here in imatinib-resistant implants. Primary GIST cell cultures for in vitro experiments and for development of more GIST cell lines are also available. Transfection into cells of these exemplary cell lines can be accomplished with either one of the following methods. (a) Transient transfection by electroporation (Eder et al., 1998). Cell suspensions (0,2 ml) will be mixed with plasmid DNA in electroporation cuvettes (0.4 cm electrode gap; Bio-Rad). Electroporation will be performed at 960 microfarads and 250 V using a Bio-Rad Gene Pulser. The cells are then transferred into complete medium. Aliquots of cells will be used to analyze the transfection effiency. (b) SN gene delivery system may be utilized (Zou et al., 2002; Li et al., 2003). It comprises a cationic liposome formulation composed of dipalmitoylethylphosphocholine, dioleoylphosphoethanolamine, dipalmitoylphospho-ethanoamine, and polyethyleneglycol. The DNA will be entrapped in the liposome using the thin-lipid film hydration method and extruded through a filter with 0.2-μm-diameter pores (Gelman Sciences; Ann Arbor, Mich.). The liposomal DNA particles will be 60-170 nm in diameter. Cells will be cultured for 24 h in six-well plates with 1 ml/well of DMEM/F12 medium with 10% FBS (Life Technologies, Inc., Gaithersburg, Md.) until 60-70% confluence was reached. The liposomal DNA (SN-DNA or Lipofectamine-DNA complex) will be directly added into the culture plates at a ratio of 2 μg of DNA/$10^6$ cells. Twenty-four hours later, the transfection efficiency will be determined.

Viability Assay: The ST882 imatinib-sensitive GIST cell line and the transfected ST882 cell line will be used to measure the cytotoxicity of imatinib at various concentrations and $LD_{50}$ of various new drugs. The thiazoly blue tetrazolium dye (MTT) assay (Cat. #2128, Sigma-Aldrich) may be utilized. Exponentially growing cell suspensions will be seeded onto 96-well microtiter plates (100 μL per well). After 24 hours of incubation at 37° C., 100 μL of each drug solution dissolved in medium at 2× concentration will be added to the existing 100 μL in the plate, bringing the final mixed concentration to the desired level. After an additional 24 hours of incubation at 37° C., 100 μL was aspirated, with care not to detach cells from the bottom of the well. Then, an additional 100 μL of drug solution dissolved in medium at 2× concentration was added, bringing the mixed concentration to the desired level. This will be repeated at 24-hour intervals for 4 days total. On day 5 (control cultures do not reach confluence), 100 μL was aspirated. 10 μL of MTT solution (5 mg/ml in PBS) will be added to the remaining 100 μL remaining in each well, and the plates will be incubated for a further 4 hours at 37° C. Then, 100 µL of MTT solubilization solution will be added to dissolve the formazan, and the solutions will be vigorously mixed. The optical density will be measured at 570 nm using the KC4 analysis program (Bio-Tek Instruments, Winoski, Vt.) for a Microsoft Windows-based computer interfaced with a Bio-Tek Microplate Reader (Cat. #EL-808; Bio-Tek, Winooski, Vt.). Each experiment will be performed using three replicate wells for each drug concentration and will be conducted independently three or four times.

Cell cycle/Apoptosis Assay: Cells in log-phase growth in 100 mm tissue culture dishes at 50% confluence will be treated with medium containing the various drugs at various concentrations or no drug (control). Cells will be treated with one dose for 24 hours or with two doses at 24-hour intervals (total 48 hours). They will be then removed from the culture dishes by trypsinization, centrifuged at 1560 g for 5 minutes, washed with PBS, and fixed for 15 minutes with 1% formaldehyde and then with 70% ethanol. Cells will be stored at –20° C. for at least 24 hours. Following fixation and incubation, cells will be washed with 1 ml of wash buffer and centrifuged at 1250 g for 15 minutes. The pellets will be resuspended and incubated overnight in 50 µL of a solution containing terminal deoxynucleotide transferase buffer and Br-dUTP (AU1001, Phoenix Flow Systems, Dan Diego, Calif.). The cells will then stained with a solution containing avidin-FITC in the dark at room temperature (Cat. #AU1001, Phoenix Flow Systems). The cells will then stained with 500 µL of propidium iodide/RNase for 30 minutes on ice (Phoenix Flow Systems). The samples will be read on a Beckman-Coulter EPICS XLMCL flow cytometer using System-2 software for two-color detection. The percentages of cells in G1, S, G2, and sub-G1 phases will be calculated using Multicycle software. Statistical analysis: The $IC_{50}$ value is defined as the concentration needed for a 50% reduction in the absorbance calculated based on the survival curves. Percent survival will be calculated as: (mean absorbance of 3 replicate wells containing drugs–mean absorbance of 3 replicate background wells)/(mean absorbance of 3 replicate drug-free wells–mean absorbance of 3 replicate background wells)×100. The effect of vehicle will be subtracted from the final value. All experiments will be performed in triplicate. Standard deviations and Student's t-test (two-tailed distribution with two-sample equal variance) will be calculated with the program in Microsoft Office 2000 Excel software.

Example 10

Multistep Genetic Events, in Addition to the Initiating Event of Kit or PDGFRA Dominant Activation Mutation, Lead to the Aggressive Phenotype in GIST In another aspect of the invention, new tumor suppressor protein(s), oncoprotein(s), and new target(s) for cancer therapy are identified. Specimens, including the primary GIST, recurrent GIST, quiescent responsive GIST and rapidly progressing imatinib-resistant GIST from the same patient, for example, are utilized for a step-wise tumorigenesis study. Comparative genome hybridization microarrays and proteomics are studied and compared. These studies will focus on new proteins and a list of tumor suppressor genes/proteins and oncogenes/oncoproteins that are located on specific chromosomes, which were reported to be abnormal by cytogenetic and LOH studies, including 1p36.1- 36.33; 14q32; 14q 23-24; 22q11.2; 22q12. Proteomics and 2-D gel electrophoresis are employed, in specific embodiments.

Example 11

Identification of Additional Resistance-Conferring Mutations

In particular embodiments of the invention, any mutation in KIT that confers resistance to imatinib is encompassed within the scope of the invention. Identification of such a mutation may occur by any means suitable in the art, such as the methods utilized as described herein for the exemplary 1982T→C mutation. There are resistance-associated KIT mutations additional to the 1982T→C mutation described herein, including D870Y, D816E, D820E, and N822K (Wardelmann et al., 2005); Y823D (Wakai et al., 2004); and T6701 (C2030T) (Tamborini et al., 2004), for example.

For example, a polynucleotide or polypeptide suspected of comprising a resistance-conferring defect in, for example KIT or PDGFR, is obtained from an individual. At least part of the polynucleotide or polypeptide is assayed for differences compared to the corresponding wild-type region or sequence, such as SEQ ID NO:29 (for KIT polynucleotide); SEQ ID NO:31 (for KIT polypeptide); SEQ ID NO:30 (for PDGFR polynucleotide); or SEQ ID NO:32 (for PDGFR polypeptide), for example. The alteration is assayed for correlation with the resistance-conferring phenotype. For example, samples from a statistically significant population are assayed for the particular alteration in question and compared to the corresponding sequence from wild-type individuals.

Example 12

Small Pool PCR in the Invention

Small pool PCR (SP-PCR) is utilized to identify and quantify the occurrence of low frequency genetic events in somatic cells. Specific embodiments may include the implementation of high throughput micro-molecular techniques, robotic technology and a new statistical approach (Coolbaugh-Murphy et al., 2004). While designed to evaluate microsatellite instability in cancer predisposition syndromes, there is an immediate major application of the procedure in evaluating patients before and during drug treatment in scenarios where somatic mutation may lead to drug resistance. The procedure allows the amplification and quantification of single DNA molecules present in complex mixtures.

In particular, small pool PCR may be used to quantitatively estimate the frequency of KIT 1982T→C mutation in pre-imatinib GIST, in specific embodiments; single-molecule and small-pool PCR (SP-PCR) procedures are known (Coolbaugh-Murphy et al., 2004; Langdon and Armour, 2003; Zhang et al., 2002). In order to estimate directly the true number of amplifiable molecules in a given volume of DNA sample, the sample is diluted to the point (generally about 1-10 pg per reaction) at which random assortment of individual target molecule in tubes is observed. PCR is then conducted on multiple (approximately 100) such small pools so that if the frequency of mutant fragments is over 1%, there is a high probability of trapping such fragments in some of the small pools. By observing the number of reactions lacking a signal (1982T→C mutation) from an allele, it is possible to estimate the mean number of the target molecules per reaction. Precautions are made to avoid false positive or contamination during DNA processing, dilution and PCR to maintain amplification fidelity. The above mentioned exemplary mutation-specific primers may be used for PCR and sequencing of the target molecule, 1982T→C mutation in KIT, for example, from each tube/reaction. Special conditions to avoid false positive reaction results are utilized.

Direct sequencing of KIT is conducted, as well as platelet derived growth factor receptor alpha (PDGFRA), in particular embodiments. These experiments identify additional mutations in KIT and PDGFRA that confer resistance to imatinib.

In specific embodiments, the single molecule quantification methodology (SP-PCR) is utilized on patients that have relapsed due to drug resistance mutations (DRMs), for example. The procedure requires very little DNA and archival material (DNA extracted from paraffin blocks or even fixed and stained slides) can be used. Current as well as archival samples collected before and during the course of treatment may be employed to allow the tracking of the origin and increase of DRMs and thereby provide knowledge of the kinetics of such drug resistance, for example. Single molecule, allele-specific PCR conducted on multiple small pools containing a series of DNA concentrations will allow a precise estimate of the frequency of cells carrying DRMs at all stages of treatment and drug resistance. In the exemplay form of cancer, GIST, the frequency of cells with DRMs prior to imatinib treatment, and tracked through the course of treatment, will be determined. This will enable the correlation of the duration of imatinib response with the DRM frequency in pre-treatment cells. The true frequency of mutation(s) that can confer imatinib resistance in pre-treatment GISTs will serve as an important "tumor marker" for prognosis and treatment decisions.

Optimization of the management of imatinib resistance using GIST cell lines as a model is performed. An in vitro model of imatinib resistance is established, such as by isolation and amplification of the cDNA harboring the resistance conferring mutation(s); subcloning in an expression vector; and transfection into imatinib-sensitive GIST cell lines to render them imatinib-resistant. Both pre-clinical study of pipeline and phase I drugs and laboratory examination of the downstream signal transduction of KIT and PDGFRA will be conducted.

Example 13

PCR Using Mutation-Specific Inner Primer

Figure 8:
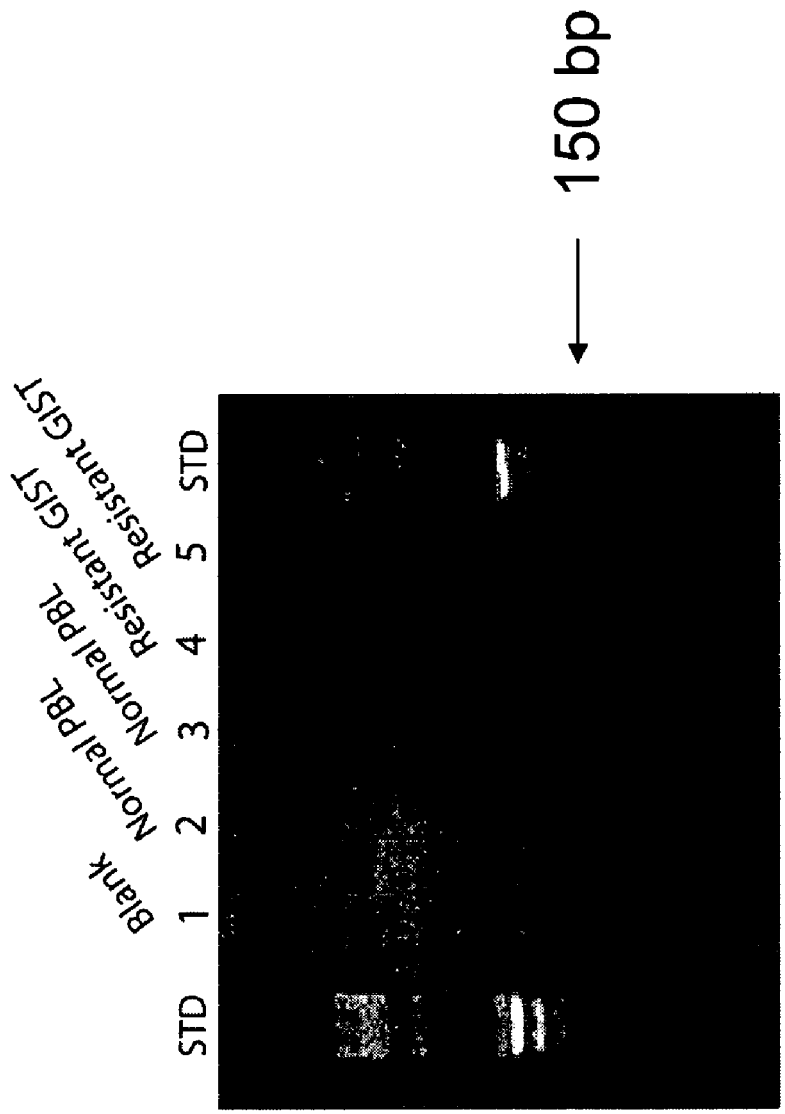
FIG. 8 demonstrates an ethidium bromide gel photo showing preferential polymerase chain reaction amplification of the mutant inner primer for the mutant DNA. STD: DNA standards; Lanes 1 (H$_2$O Blank): control using water; Lanes 2-3 (normal PBL): normal control using DNA extracted from normal human (age and sex matched) peripheral blood lymphocytes; Lanes 4-5 (Imatinib-resistant GIST): DNA extracted from an imatinib-resistant GIST. A strong band (150 bp) indicating robust amplification from the tumor mutant DNA is detected (lanes 4-5), yet no visible product can be visualized from the normal PBL DNA (lanes 2-3).

In specific embodiments of the invention, the "C" for "T" substitution in the inner primer (FIG. 7, yellow highlight in the middle box) would efficiently anneal with the mutant gene harboring the specific novel mutation of 1982 T→C in KIT in GIST. When annealing to the normal gene, this primer would form a mismatch "bubble" at the 3' end, and hence would be amplified far less efficiently or not amplified at all depending on the stringency of the PCR conditions. The present inventors have identified conditions (see elsewhere herein) under which only the mutant gene would amplify preferentially using the specially-designed inner primer (FIG. 7) and provided significant evidence, as shown in FIG. 8. There was robust amplification from the tumor DNA, yet there was minimal product produced from the normal peripheral blood lymphocytes (PBLs) DNA (FIG. 8), demonstrating the specificity.

In specific embodiments of the invention, PCR is done in a hemi-nested fashion (see FIG. 7 for exemplary primer sequences.) The primary PCR amplification reaction includes the following: the reaction mixture comprises 1× GeneAmp buffer (ABI), 1.5 mM MgCl$_2$ (Sigma), 1 µM each Forward Outer primer (FO, FIG. 7) and Reverse Inner/Outer primer (RIO, FIG. 7), 1 U AmpliTaq Gold polymerase (ABI) and 10 genome equivalents of DNA (60 pg of DNA) in a final volume of 12 µl per reaction; cycle times were 95° C.×7 min, [(95° C.×30 s, 52° C.×30 s, 71° C.×40 s)×35 cycles], 72° C.×7 min, hold at 8° C. The secondary PCR amplification reaction includes the following: the primary amplification products (275 bp) were diluted 10-fold, 2 µl was used as template in the secondary amplification reaction, which had the same composition as the primer PCR, except the Forward Outer primer is replaced with the Mutation-specific Forward Inner (Mutation FI, FIG. 7); cycle times for the secondary reaction with the mutant primer were 95° C.×7 min, [(95° C.×30 s, 62° C.×30 s, 7° C.×40 s)×37 cycles], 72° C.×7 min, hold at 8° C. The cycle times for the Wild-type Forward Inner primer (Wild-type-FI, FIG. 7) in the secondary PCR is identical to that for the mutant primer, except that annealing temperature is 59° C., and it is amplified for only 35 cycles. The PCR products were separated in 2% agarose gel electrophoresis, visualized by Ethidium Bromide and UV transluminator.

Example 14

Small Pool PCR (SP-PCR) for Quantification of Mutant Frequency

The molecular concept is described briefly. In SP-PCR, DNA was diluted to varying concentrations and delivered into over 100 wells of a microtest plate such that each well (or small pool) contained less than a single genome equivalent (g.e.) of DNA. Nested PCR using fluorescently labeled inner primers specific for the mutant allele was then conducted. Therefore, infrequent (1%-25%) mutant fragments captured in one or more of the small pools would not be overwhelmed by progenitor fragments and could be readily amplified, identified, and counted.

Coolbaugh-Murphy et al. (2004) developed exemplary robotic, multiplexing and statistical procedures for efficient SP-PCR for sensitive and quantitative analysis of microsatellite instability (MSI) in somatic tissues. Single molecules could be amplified and frequency determinations in complex mixtures determined.

Figure 9:
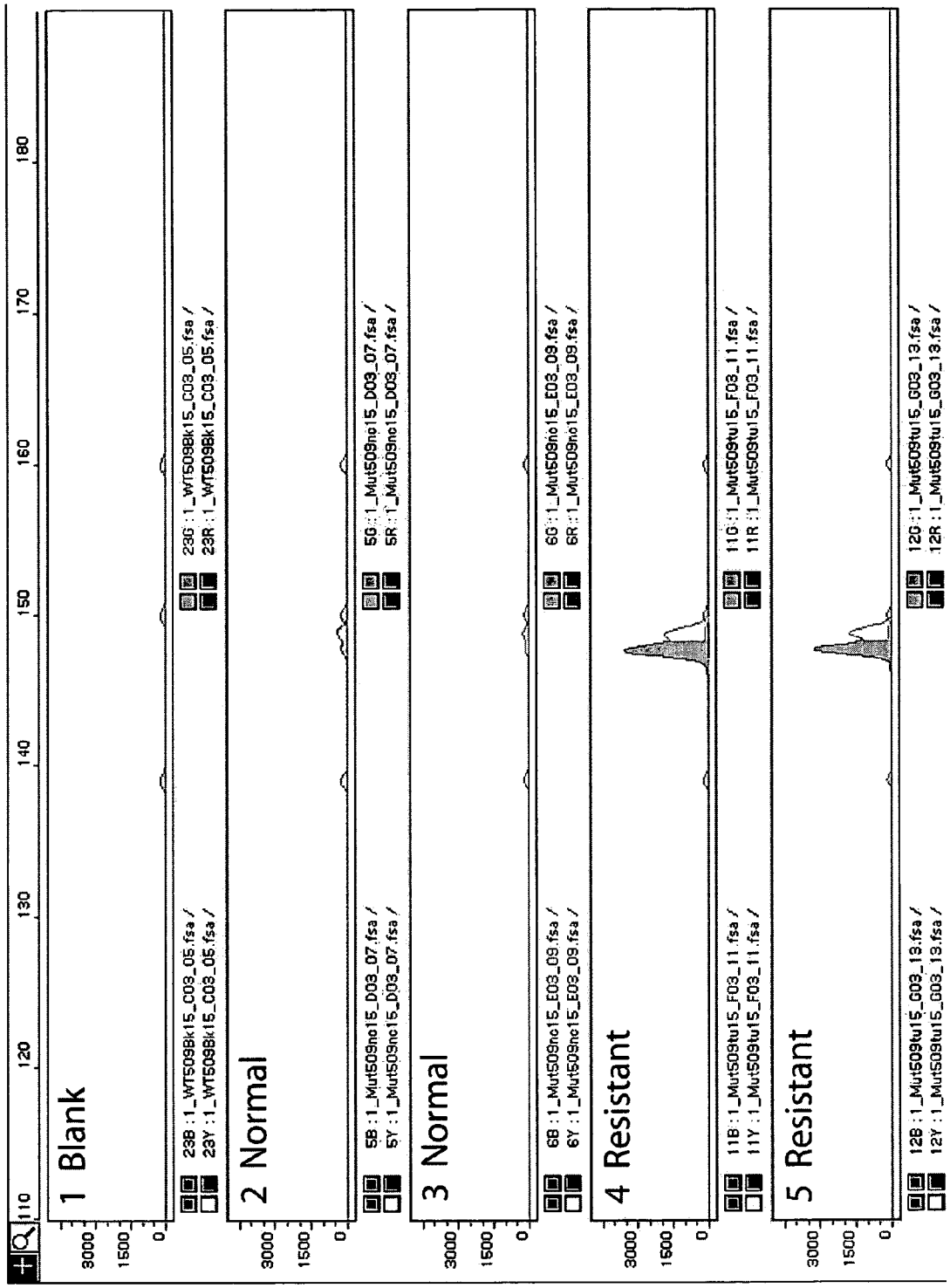
FIG. 9 provides chromatograms showing fluorescently-labeled polymerase chain reaction products. The Mutation-specific Forward Inner (Mutation FI) and the Wild type Forward Inner (Wild type-FI) primers were fluorescently labeled at the 5'end with 6-FAM and NED, respectively; hemi-nested PCR using these fluorescently labeled Forward Inner primers, and Reverse Inner/Outer primer (RIO) were then conducted. The multiplexed fluorescently labeled PCR products were analyzed on the ABI 3100 (ABI, Foster City, Calif.). Panel 1 (Blank): control using H$_2$O. Panels 2-3 (Normal): using the same primers on 100 genome equivalent (g.e.) of DNA from the PBLs of normal individuals that produced no signal. Panels 4-5 (Resistant): using the same primers on 10 g.e. of DNA from a imatinib-resistant GIST containing the mutation of 1982 T→C in KIT produced a robust signal at a single peak of 150 bp.

The present inventors adopted the procedure to detect the frequency of mutant KIT alleles harboring the specific novel mutation of 1982 T→C in KIT in either normal tissue or GIST. The Mutation-specific Forward Inner (Mutation FI) and the Wild-type Forward Inner (Wild-type-FI) were fluorescently labeled at the 5'end with 6-FAM and NED, respectively; hemi-nested PCR using these fluorescently labeled Forward Inner primers and Reverse Inner/Outer primer (RIO) was then conducted. The nested PCR procedures were optimized for the amplification of such mutant alleles when only a single g.e. of mutant DNA is present. Specifically the present inventors have conducted nested PCR using the mutant specific inner primers on 10 g.e. of imanitib-resistant GIST DNA and examined the fluorescent PCR products using ABI 3100 (FIG. 9). There was a robust signal at a single peak of 150 bp (FIG. 9) harboring the specific novel mutation of 1982 T→C in KIT. This indicated that there would be no difficulty in identifying such fragments at single g.e. In the same run, using the same primers on 100 g.e. of DNA from the PBLs of normal individuals, produced no signal (FIG. 9). These data verify that the system will specifically detect single mutant fragments when present in 100 g.e. of test DNA.

Therefore, when present at low frequency, say 0.1%, by putting 100 g.e. of target DNA into each of over 100 wells of a microtest plate and conducting nested PCR followed by ABI analysis of any fluorescent products amplified in any of the wells, in specific embodiments of the invention product will be identified in approximately 10 wells.

In particular aspects of the invention, this method of SP-PCR is better than real time PCR, because it will detect fragments at single g.e. of DNA, whereas real time PCR requires more than 10 g.e. of DNA to get a result.

Statistical Analysis

In SP-PCR, the data comprises whether or not the mutant allele was seen in every small pool. An exemplary model in which the number of alleles in replicate pools were distributed Poisson, and in which particular allele frequencies constituted a fixed proportion of the total, has been described (Coolbaugh-Murphy et al., 2004). Maximum likelihood estimates of the mean number of alleles in each pool and the frequencies of each allele were derived. The mutant frequencies were compared between groups for significance using the arc-sin transformed mutant frequencies and the bootstrap standard error. Similar or identical models may be employed in the invention.

Example 15

Significance of the Present Invention

The present invention provides the novel association between rapidly progressive imatinib-resistant GIST after initial near complete response to treatment and mutation in KIT kinase domain 1. In leukemia, the imatinib-resistant clones are mixed with imatinib sensitive clones and normal bone marrow and blood, whereas in GIST, individual implants are distinct (FIG. 1) and can be closely monitored by CT and PET scans, so immediate biopsy or surgical removal of specific imatinib-resistant clone is possible. This unique feature provides convincing evidence for the temporal relationship between emergence of resistance in vivo and evolution of this new KIT mutation identified in exon 13. Normal karyotype is not an uncommon finding in GISTs in the laboratory of the present inventors and in literature (Sandberg and Bridge, 2002; Heinrich et al., 2002; Debiec-Rychter et al., 2001). In comparison to leukemia, GIST is a relatively slow growing tumor without excessive chromosome instability. To date, no untreated GISTs have been reported with more than one mutation in KIT, so finding a second and new KIT mutation in closely monitored imatinib-resistant clones is convincing in vivo evidence of causal relationship.

Allelic specific sequencing analyses show that this novel KIT exon 13 missense mutation, 1982T→C, occurs in the original mutated allele, not in the normal allele. One possible explanation could be attributed to the local regional genetic instability of the allele that harbor exon 11 or exon 9 mutation predisposing it to a second hit of an additional mutation in the same allele. Under the selection pressure of imatinib treatment, the second possible explanation can be attributed to the preferential proliferative advantage of the clones that harbor the dominant activating exon 11 or exon 9 mutation plus second hit of 1982T→C mutation in the same allele, which may acquire significantly more advantage in imatinib resistance than those clones that harbor second hit of the 1982T→C mutation in the normal allele. These two possibilities are not mutually exclusive.

Val654 is in KIT kinase domain 1 and is conserved among ABL, src, hck, PDGFRα and KIT. The crystal structure of KIT has recently been reported (Mol et al., 2003). A schema (FIG. 3) showing the structural and functional regions of KIT is included as a reference, and the crystal structure with some relevant mutations, including Val654Ala, is provided in FIG. 6. The first residue of the KIT ATP phosphate-binding loop (P-loop) is Gly596 (Mol et al., 2003; Azam et al., 2003), which is 58 amino acids N-terminal to this novel Val654Ala mutation. In close proximity to Val654Ala, are the imatinib contact points, Glu640, Thr670, Cys673, Asp810 (Fabbro et al., 2002; Manley et al., 2002) and the ADP binding residues, Glu671, Cys673 (Mol et al., 2003) and Lys623. The conserved Glu640 in control helix (C-helix), a single α-helix, forms a critical interaction with the side chain of Lys623, which binds ADP. By structural analysis, this new mutation, Val654Ala, therefore most likely produces allosteric conformational changes that alter the the configuration of KIT kinase domain and the relative affinity of KIT to imatinib.

Kinase domain mutations in ABL in leukemia have almost always been associated with imatinib resistance (Azam et al., 2003; Gorre et al., 2001; von Bubnoff et al., 2002; Hochhaus et al., 2002; Roche-Lestienne et al., 2002; Shannon, 2002; Shah et al., 2002; Gambacorii-Passerini et al., 2003). The most frequent ABL mutation sites in imatinib-resistant leukemia patients are Glu255Lys (274 in ABL Ib), Thr315Ile (334 in ABL Ib) and Met351Thr (370 in ABL Ib) (Gorre et al. 2001; von Bubnoff et al., 2002; Hochhaus et al., 2002), which are 6 to 102 amino acids C-terminal to the first amino acid residue in P-loop.

Some of the ABL mutations that confer imatinib resistance in leukemia were found to be present in leukemia patients prior to imatinib treatment (Roche-Lestienne et al., 2002; Shannon, 2002; Shah et al., 2002). The novel mutation, Val654Ala, which has never been reported in literature before, was not detectable in any pre-imatinib GISTs or any quiescent implants by polymerase chain reaction (Table 1, using primer #3 for genomic DNA and primer #7 for cDNA sequence) indicating that the mechanism of imatinib resistance in clones 1, 2, 4, 5, 8, 11 in patients A-E is either due to development of a new mutation or imatinib selection of extremely low level of pre-existing clones that harbor this mutation prior to treatment.

As GISTs are initiated by constitutive KIT signal, hence KIT is an ideal target for therapy as evidenced by the dramatic and immediate effect of imatinib (FIG. 1a-1-4, 1a-7-8, 1b-1-2). For the same reason, it is also conceivable that a single missense mutation in kinase domain in KIT is sufficient to result in imatinib resistance and unleash the proliferative constraints. The first report of imatinib-resistant CML (Gorre et al. 2001) showed that 6 out of 9 patients harbored a mutation with a single amino acid substitution in ABL that confers imatinib resistance. Later, more mutations in different region of ABL were discovered. Here, we identified a novel single amino acid substitution in KIT in 6 separate implants from 5 out of 5 (100%) imatinib-resistant rapidly progressing GIST patients. The 12 GIST patients presented in Table 2 underwent surgery at different times, spanned over 24 months and nucleotide sequence analyses were performed shortly after each surgery at different times and hence cross contamination is unlikely. In addition, the present inventors obtained different exon 11 mutations in patients A-D and J-L, which provides direct proof against any cross contamination.

REFERENCES

All patents and publications mentioned in the specification are indicative of the level of those skilled in the art to which the invention pertains. All patents and publications are herein incorporated by reference herein in their entirety to the same extent as if each individual publication was specifically and individually indicated to be incorporated by reference.

Allander, S. V., Nupponen, N. N., Ringnér, M., Hostetter, G., Maher, G. W., Goldberger, N., Chen, Y., Carpten, J., Elkahloun, A. G., and Meltzer, P. S. Gastrointestinal Stromal Tumors with KIT Mutations Exhibit a Remarkably Homogeneous Gene Expression Profile1. Cancer Res, 61: 8624-8628, 2001.

Azam, M., Latek, R. R., and Daley, G. Q. Mechanisms of Autoinhibition and STI571/Imatinib Resistance Revealed by Mutagenesis of BCR-ABL. Cell, 112: 831-843, 2003.

Chan, P. M., Ilangumaran, S., La Rose, J., Chakrabartty, A., and Rottapel, R. Autoinhibition of the Kit Receptor Tyrosine Kinase by the Cytosolic Juxtamembrane Region. Mol Cell Biol, 23: 3067-3078, 2003.

Chen L L, Trent J C, Wu, E F, et al.: A missense mutation in KIT kinase domain 1 correlates with imatinib resistance in gastrointestinal stromal tumors. Cancer Res 2004, 64:5913-5919.

Coolbaugh-Murphy, M., Maleki, A., Ramagli, L., Frazier, M., Lichtiger, B., Monckton, D. G., Siciliano, M. J., and Brown, B. W. Estimating allele frequencies by small pool PCR. Genomics, 84:419-430.

Corless, C. L., McGreevey, L., Haley, A., Town, A., and Heinrich, M. C. KIT Mutations Are Common In Incidental Gastrointestinal Stromal Tumors One Centimeter or Less in Size. AM J Pathol, 160: 1567-1572, 2002.

Crosier, P. S., Ricciardi, S. T., Hall, L. R., Vitas, M. R., Clark, S. C., and Crosier, K. E. Expression of Isoforms of the Human Receptor Tyroisine Kinase c-kit in Leukemic Cell Lines and Acute Myeloid Leukemia. Blood, 82: 1151-1158, 1993.

Debiec-Rychter, M., Lasota, J., Sarloma-Rikala, M., Kordek, R., and Miettinen, M. Chromosomal aberrations in malignant gastrointestinal stromal tumors: correlation with c-KIT gene mutation. Cancer Genet and Cytogenet, 128: 24-30, 2001.

Demetri, G. D., von Mehren, M., Blanke, C. D., Van den Abbeele, A. D., Eisenberg, B., Roberts, P. J., Heinrich, M. C., Tuveson, D. A., Singer, S., Janicek, M., Fletcher, J. A., Silverman, S. G., Silberman, S. L., Capdeville, R., Kiese, B., Peng, B., Dimitrijevic, S., Druker, B. J., Corless, C., Fletcher, C. D. M., and Joensuu, H. Efficacy and Safety of Imatinib Mesylate in Advanced Gastrointestinal Stromal Tumors. N Engl J Med, 347: 472-480, 2002.

Eder, A. M., Dominguez, L., Franke, T. F., and Ashwell, J. D. Phosphoinositide 3-Kinase Regulation of T Cell Receptor-mediated Interleukin-2 Gene Expression in Normal T Cells. J Biol Chem, 273: 28025-28031, 1998.

Fabbro, D., Ruetz, S., Buchdunger, E., Cowan-Jacob, S. W., Fendrich, G., Liebetanz, J., Mestan, J., O'Reilly, T., Traxler, P., Chaudhuri, B., Fretz, H., Zimmermann, J., Meyer, T., Caravatti, G., Furet, P., and Manley, P. W. Protein kinases as targets for anticancer agents: from inhibitors to useful drugs. Pharmacol Ther, 93: 79-98, 2002.

Gambacorti-Passerini, C. B., Gunby, R. H., Piazza, R., Galieta, A., Rostagno, R., and Scapozza, L. Molecular mechanisms of resistance to imatinib in Philadelphia-chromosome-positive leukaemias. Lancet Oncol, 4: 75-85, 2003.

Gorre, M. E., Mohammed, M., Ellwood, K., Hsu, N., Paquette, R., Rao, P. N., and Sawyers, C. L. Clinical resistance to STI-571 cancer therapy caused by BCR-ABL gene mutation or amplification. Science, 293: 876-880, 2001.

Guex N, Peitsch M C: SWISS-MODEL and the Swiss-PdbViewer: an environment for comparative protein modeling. Electrophoresis 1997, 18:2714-2723.

Heinrich, M. C., Blanke, C. D., Druker, B. J., and Corless, C. L. Inhibition of KIT Tyrosine Kinase Activity: A Novel Molecular Approach to the Treatment of KIT-Positive Malignancies. J Clin Oncol, 20: 1692-1703, 2002.

Heinrich, M. C., Corless, C. L., Deunsing, A., McGreevey, L., Chen, C., Joseph, N., Singer, S., Griffith, D., Haley, A., Town, A., Demetri, G. D., Fletcher, C. D. M., and Fletcher, J. A. PDGFRA Activating Mutations in Gastrointestinal Stromal Tumors. Science, 299: 708-710, 2003.

Heinrich, M. D., Corless, C. L., Demetri, G. D., Blank, C. D., von Mehren, M., Joensuu, H., McGreevey, L. S., Chen, C., Van den Abbeele, A. D., Druker, B. J., Kiese, B., Eisenberg, B., Roberts, P. J., Singer, S., Fletcher, C. D. M., Silberman, S., Dimitrijevic, S., and Fletcher, J. A. Kinase Mutation and Imatinib Response in Patients with Metastatic Gastrointestinal Stromal Tumor. J. Clin Oncol, 21: 4342-4349, 2003.

Hirota, S., Isozaki, K., Moriyama, Y., Hashimoto, K., Nishida, T., Ishiguro, S., Kawano, K., Hanada, M., Kurata, A., Takeda, M., Tunio, G. M., Matsuzawa, Y., Kanakura, Y., Shinomura, Y., and Kitamura, Y. Gain-of-Function Mutations of c-kit in Human Gastrointestinal Stromal Tumors. Science, 279: 577-580, 1998.

Hirota, S., Nishida, T., Isozaki, K., Taniguchi, M., Nakamura, J., and Okazaki, T. Gain-of-function mutation at the extracellular domain of KIT in gastrointestinal stromal tumors. J Pathol, 193: 505-510, 2001.

Hirota, S., Nishida, T., Isozaki, K., Taniguchi, M., Nishikawa, K., Ohashi, A., Takabayashi, A., Obayashi, T., Okuno, T., Kinoshita, K., Chen, H., Shinomura, Y., and Kitamura, Y. Familial Gastrointestinal Stromal Tumors Associated With Dysphagia and Novel Type Germline Mutation of KIT Gene. Gastroenterology, 122: 1493-1499, 2002.

Hirota, S., Ohashi, A., Nishida, T., Isozaki, K., Kinoshita, K., Shinomura, Y., and Kitamura, Y. Gain-of-Function Mutations of Platelet-Derived Growth Factor Receptor □ Gene in Gastrointestinal Stromal Tumors. Gastroenterology, 125: 660-667, 2003.

Hochhaus, A., Kreil, S., Corbin, A. S., La Rosee, P., Muller, M. C., Lahaye, T., Hanfstein, B., Schoch, C., Cross, N. C. P., Berger, U., Gschaidmeier, H., Druker, B. J., and Hehlmann, R. Molecular and chromosomal mechanisms of resistance to imatinib (STI571) therapy. Leukemia, 16: 2190-2196, 2002.

Kinoshita, K., Isozaki, K., Hirota, S., Nishida, T., Chen, H., Nakahara, M., Nagasawa, Y., Ohashi, A., Shinomura, Y., Kitamura, Y., and Matsuzawa, Y. c-kit Gene mutation at exon 17 or 13 is very rare in sporadic gastrointestinal stromal tumors. J Gastroenterol Hepatol, 18: 147-151, 2003.

Kitamura, Y., Hirota, S., and Nishida, T. Gastrointestinal stromal tumors (GIST): A model for molecule-based diagnosis and treatment of solid tumors. Cancer Sci, 94: 315-320, 2003.

Langdon, J. A. and Armour, J. A. L. Evolutionn and population genetics of the H-ras minisatellite and cancer predisposition. Hum Mol Genet, 12: 891-900, 2003.

Lasota, J., Wozniak, A., Sarloma-Rikala, M., Rys, J., Kordek, R., Nassar, A., Sobin, L. H., and Miettinen, M. Mutations in Exons 9 and 13 of KIT Gene Are Rare Events in Gastrointestinal Stromal Tumors. Am J Pathol, 157: 1091-1095, 2000.

Li, Y. M., Wen, Y., Zhou, B. P., Kuo, H. P., Ding, Q., and Hung, M. C. Enhancement of Bik antitumor effect by Bik mutants. Cancer Res. 63:7630-7633, 2003.

Lux, M. L., Rubin, B. P., Biase, T. L., Chen, C., Maclure, T., Demetri, G., Xiao, S., Singer, S., Fletcher, C. D. M., and Fletcher, J. A. KIT Extracellular and Kinase Domain Mutations in Gastrointestinal Stromal Tumors. Am J Pathol, 156: 791-795, 2000.

Ma, Y., Cunningham, M. E., Wang, X., Ghosh, I., Regan, L., and Longley, B. J. Inhibition of Spontaneous Receptor Phosphorylation by Residues in a Putative α-Helix in the KIT Intracellular Juxtamembrane Region. J Biol Chem, 274: 13399-13402, 1999.

Manley, P. W., Cowan-Jacob, S. W., Buchdunger, E., Fabbro, D., Fendrich, G., Furet, P., Meyer, T., and Zimmermann, J. Imatinib: a selective tyrosine kinase inhibitor. Eur J Cancer, 38: S19-S27, 2002.

Mol, C. D., Lim, K. B., Sridhar, V., Zou, H., Chien, E. Y. T., Sang, B., Nowakowski, J., Kassel, D. B., Cronin, C. N., and McRee, D. E. Structure of c-Kit Product Complex Reveals the Basis for Kinase Transactivation. J Biol Chem, 278: 31461-31464, 2003.

Mol C D, Dougan D R, Schneider T R, et al.: Structural basis for the autoinhibition and STI-571 inhibition of c-kit tyrosine kinase. J Biol Chem 2004, 279:31655-31663.

Raspollini, M. R., Amunni, G., Villanucci, A., Baroni, G., Taddei, A., and Taddei, G. L. c-KIT expression and correlation with chemotherapy resistance in ovarian carcinoma: an immunocytochemical study. Ann. Oncol. 15:594-597, 2004.

Roche-Lestienne, C., Soenen-Comu, V., Grardel-Duflos, N., Lai, J., Phillipe, N., Facon, T., Fenaux, P., and Preudhomme, C. Several types of mutations of the Abl gene can be found in chronic myeloid leukemia patients resistant to STI571, and they can pre-exist to the onset of treatment. Blood, 100: 1014-1018, 2002.

Rubin, B. P., Singer, S., Tsao, C., Duensin, A., Lux, M. L., Ruiz, R., Hibbard, M. K., Chen, C., Xiao, S., Tuveson, D. A., Demetri, G. D., Fletcher, C. D. M., and Fletcher, J. A. KIT Activation Is a Ubiquitous Feature of Gastrointestinal Stromal Tumors. Cancer Res, 61: 8118-8121, 2001.

Sakurai, S., Oguni, S., Hironaka, M., Fukayama, M., Morinaga, S., and Saito, K. Mutations in c-kit gene exons 9 and 13 in gastrointestinal stromal tumors among Japanese. Jpn J Cancer Res, 92: 494-498, 2001.

Sandberg, A. A., and Bridge, J. A. Updates on the cytogenetics and molecular genetics of bone and soft tissue tumors: gastrointestinal stromal tumors. Cancer Genet and Cytogenet, 135: 1-22, 2002.

Shah, N. P., Nicoll, J. M., Nagar, B., Gorre, M. E., Paquette, R. L., Kuriyan, J., and Sawyers, C. L. Multiple BCR-ABL kinase domain mutations confer polyclonal resistance to the tyrosine kinasae inhibitor imatinib (STI571) in chronic phase and blast crisis chronic myleoid leukemia. Cancer Cell, 2: 117-125, 2002.

Shannon, K. M. Resistance in the land of molecular cancer therapeutics. Cancer Cell, 2: 99-102, 2002.

Sommer, G., Agosti, V., Ehlers, I., Rossi, F., Corbacioglu, S., Farkas, J., Moore, M., Manova, K., Antonescu, C., and Besmer, P. Gastrointestinal stromal tumors in a mouse model by targeted mutation of the Kit receptor tyrosine kinase. Proc Natl Acad Sci, 100: 6706-6711, 2003.

Tamborini E, Bonadiman L, Greco A, et al.: A new mutation in the KIT ATP pocket causes acquired resistance to imatinib in a gastrointestinal stromal tumor patient. Gastroenterology 2004, 127:294-299.

Tuveson, D. A., Willis, N. A., Jacks, t., Griffin, J. D., Siner, S., Fletcher, D. C. M., Fletcher, J. A., Demetri, G. D. STI571 inactivation of the gastrointestinal stromal tumor c-KIT oncoprotein: biological and clinical implications. Oncogene, 20:5054-5058, 2001.

von Bubnoff, N., Schneller, F., Perschel, C., and Duyster, J. BCR-ABL gene mutations in relation to clinical resistance of Philadelphia-chromosome-positive leukaemia to STI571: a positive study. Lancet, 359: 487-491, 2002.

Wardelmann, E., Thomas, N., Merkelbach-Bruse, s., Pauls, K., Speidel, N., Buttner, r., Bihl, H., Leutner, C. C., Heinicke, T., Hohenberger, P. Acquired resistance to imatinib in gastrointestinal stromal tumours caused by multiple KIT mutations. Lancet Oncol. 6(4):249-51, 2004.

Wakai T, Kanda T, Hirota S, et al.: Late resistance to imatinib therapy in a metastatic gastrointestinal stromal tumour is associated with a second KIT mutation. Br J Cancer, 90: 2059-2061, 2004.

Zhang, Y., Monckton, D. G., Siciliano, M. J., Connor, T. H., and Meistrich, M. L. Age and insertion site dependence of repeat number instability of a human DM1 transgene in individual mouse sperm. Hum Mol Genet, 11: 791-798, 2002.

Zhu, W. M., Dong, W. F., and Minden, M. Alternate Splicing Creates Two Forms of the Human Kit Protein. Leukemia and Lymphoma, 12: 441-447, 1993.

Zou, Y., Peng, H., Zhou, B., Wen, Y., Wang, S. C., Tsai, E. M., and Hung, M. C. Systemic tumor suppression by the proapototic gnen bik. Cancer Res., 62: 8-12, 2002.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of screening an individual for imatinib resistance or a predisposition thereto, wherein the individual has a cancer characterized by having at least one cell comprising a c-KIT polynucleotide, the method comprising determining the presence of a T->C mutation at nucleotide position 1982 of the KIT gene, said nucleotide position defined according to the KIT gene nucleotide sequence of SEQ ID NO:29, in a sample obtained from the cancer of said individual, wherein the presence of such a mutation indicates the individual exhibits imatinib resistance or a predisposition thereto.

2. The method of claim 1, wherein the cancer is a gastrointestinal stromal tumor or a metastasis thereof.

3. The method of claim 1, wherein the sample from the individual is comprised in paraffin or is frozen.

4. The method of claim 1, wherein the sample from the individual comprises fluid, cell, tissue, or a combination thereof.

5. The method of claim 1, wherein the determining the presence of the mutation is further defined as assaying said sample by a polymerase chain reaction using one or more polynucleotide primers.

6. The method of claim 5, wherein the polymerase chain reaction is small-pool polymerase chain reaction.

7. The method of claim 5, wherein the polymerase chain reaction utilizes a primer that would amplify a polynucleotide sequence comprising the mutation or a complement thereof.

8. The method of claim 1, further defined as assaying RNA for the mutation.

9. The method of claim 1, further defined as assaying the KIT gene for the mutation.

10. The method of claim 1, wherein the cancer is an ovarian cancer.

11. The method of claim 5, wherein the one or more polynucleotide primers are associated with a substrate.

12. The method of claim 11, wherein the substrate is a microchip.

* * * * *